United States Patent
Rajendran

(10) Patent No.: US 11,931,390 B1
(45) Date of Patent: Mar. 19, 2024

(54) COMPOSITIONS AND METHODS FOR IMMUNE HEALTH

(71) Applicant: KARALLIEF INC, Boston, MA (US)

(72) Inventor: Krishna Rajendran, Boston, MA (US)

(*) Notice: Subject to any disclaimer, the term of this patent is extended or adjusted under 35 U.S.C. 154(b) by 0 days.

(21) Appl. No.: 18/336,575

(22) Filed: Jun. 16, 2023

(51) Int. Cl.
| | |
|---|---|
| *A61K 36/19* | (2006.01) |
| *A61K 9/00* | (2006.01) |
| *A61K 31/365* | (2006.01) |
| *A61K 31/56* | (2006.01) |
| *A61K 31/585* | (2006.01) |
| *A61K 31/7048* | (2006.01) |
| *A61K 36/185* | (2006.01) |
| *A61K 36/53* | (2006.01) |
| *A61K 36/81* | (2006.01) |
| *A61K 45/06* | (2006.01) |
| *A61P 11/00* | (2006.01) |

(52) U.S. Cl.
CPC ............ *A61K 36/19* (2013.01); *A61K 9/0053* (2013.01); *A61K 31/365* (2013.01); *A61K 31/56* (2013.01); *A61K 31/585* (2013.01); *A61K 31/7048* (2013.01); *A61K 36/185* (2013.01); *A61K 36/53* (2013.01); *A61K 36/81* (2013.01); *A61K 45/06* (2013.01); *A61P 11/00* (2018.01)

(58) Field of Classification Search
None
See application file for complete search history.

(56) References Cited

PUBLICATIONS

Adiguna et al., :Antiviral Activities of Andrographolide and Its Derivatives: Mechanism of Action and Delivery System, Pharmaceuticals 2021, 14, 1102.
Almatroodi et al., "Osmium sanctum: Role in Diseases Management Through Modulating Various Biological Activity", Pharmacogn J. 2020; 12(5): 1198-1205.
Chen et al., "Activity of Andrographolide and Its Derivatives against Influenza Virus in Vivo and in Vitro", Biol. Pharm. Bull. 32(8) 1385-1391 (2009).
Chih-Chun Wen et al., "Developing Phytocompounds from Medicinal Plants as Immunomodulators", Advances in Botanical Research, vol. 62 0065-2296/12.
Chow et al., Abstract, "Inhalable neutralizing antibodies-promising approach to combating respiratory viral infections", Trends Pharmacological Sciences, Feb. 2023;44(2):85-97.
D D Caceres et al., "Use of visual analogue scale measurements (VAS) to assess the effectiveness of standardized Andrographis paniculata extract SHA-10 in reducing the symptoms of common cold. A randomized double blind-placebo study", Phytomedicine. 1999;6(4):217-223.
Dehn Lunn A, "Reducing inappropriate antibiotic prescribing in upper respiratory tract infection in a primary care setting in Kolkata, India", BMJ Open Quality 2018;7:e000217.
H. Zhang et al., "Effect of fermented milk on upper respiratory tract infection in adults who lived in the haze area of Northern China: A randomized clinical trial", Pharmaceutical Biology 2021, vol. 59, No. 1, 645-650.
Khan et al., "Recent advances in medicinal plant biotechnology", Indian Journal of Biotechnology; vol. 8, Jan. 2009, pp. 9-22.
Logambal et al., Abstract, "Immunostimulatory effect of leaf extract of *Ocimum sanctum* Linn. in Oreochromis mossambicus (Peters)", Jan. 2000, Hydrobiologia, 430, 113-120.
Melbye H, Hvidsten D, Holm A, et al., "The course of C-reactive protein response in untreated upper respiratory tract infection", British Journal of General Practice, Sep. 2004, 54, 653-658.
Mueller et al., Immune responses to viruses, Clinical Immunology, 2008: 421-431.
N. Jain R. Lodha and S.K. Kabra, "Upper Respiratory Tract Infections", Indian Journal of Pediatrics, vol. 68, Dec. 2001.
Namrata Gangal et al., "Reconsidering Traditional Medicinal Plants to Combat COVID19", AIJR Reprints, 34, Version 1, 2020.
Nijkamp et al., "Principles of Immunopharmacology", Croat Med J 2007;48:271-275.
Pan et al., "Traditional Medicines in the World: Where to Go Next?", Evidence-Based Complementary and Alternative Medicine vol. 2014, Article ID 739895, 4 pages.
Ponticelli et al., "Specialized metabolites from plants as a source of new multi-target antiviral drugs: a systematic review", Phytochemistry Reviews, DOI: https://doi.org/10.1007/s11101-023-09855-2.
S. J. Stohs and Hartman, "Review of the Safety and Efficacy of Moringa oleifera", Phytother. Res. 29: 796-804 (2015).
S. Mondal et al., "Mondal Double-blinded randomized controlled trial for immunomodulatory effects of Tulsi (*Ocimum sanctum* Linn.) leaf extract on healthy volunteers".
S.A.Heinz et al., "Quercetin supplementation and upper respiratory tract infection: A randomized community clinical trial" PharmacologicalResearch62 (2010) 237-242.
Saeidnia et al., Abstract, "Reverse pharmacognosy and reverse pharmacology; two closely related approaches for drug discovery development", Current pharmaceutical biotechnology, 2016;17(11):1016-1022.
Singh & Majumdar, "Evaluation of antiinflammatory activity of fatty acids of Ocimum sanctum fixed oil", Indian Journal of Experimental Biology 1997;35:380-3.

(Continued)

*Primary Examiner* — Michael V Meller
(74) *Attorney, Agent, or Firm* — Stonebridge IP, PLLC

(57) ABSTRACT

A composition includes *Andrographis paniculata* extract at about 20% to about 30% by weight of the total composition; *Withania somnifera* extract at about 16% to about 24% by weight of the total composition; *Moringa oleifera* extract at about 24% to about 36% by weight of the total composition; and *Ocimum sanctum* extract at about 20% to about 30% by weight of the total composition. The composition may be in the form of a capsule, a pill, or a tablet. A method of supporting, maintaining, or improving immunity in a mammal includes administering the composition to a mammal, where upper respiratory tract infection symptoms are reduced, concentration of C-Reactive protein in the blood of the mammal is decreased, or the concentration of Immunoglobulin G in the blood of the mammal is increased. The mammal may be a human. The improved immunity may be to a virus. The improved immunity may be to an upper respiratory tract infection.

11 Claims, 17 Drawing Sheets

(56) References Cited

PUBLICATIONS

Singh et al., Abstract "Chemical and pharmacological studies on fixed oil of Ocimum sanctum", Indian Journal of Experimental Biology 1996;34:1212-5.
Somerville et al., "Effect of flavonoids on upper respiratory tract infections and immune function a systematic review and meta-analysis", American Society for Nutrition, Adv. Nutr. 2016;7:488-97.
Thamlikitkul et al., Abstract "Efficacy of Andrographis Paniculata, Nees for Pharyngotonsillitis in Adults", Journal of the Medical Association of Thailand. 1991;74 (10):437-442.
Tharakan et al., "Immunomodulatory Effect of Withania Somnifera (Ashwagandha) Extract—A Randomized, Double-Blind, Placebo Controlled Trial with an Open Label Extension on Healthy Participants", J. Clin Med. Oct. 2021, 3644.
Wikipedia, "Active ingredient", the free encyclopedia, retrieved on May 24, 2023.
Wikipedia, "Andrographis paniculata", the free encyclopedia, retrieved on May 24, 2023.
Wikipedia, "Moringa oleifera", the free encyclopedia, retrieved on May 24, 2023.
Wikipedia, "Ocimum tenuiflorum", the free encyclopedia, retrieved on May 24, 2023.
Wikipedia, "Tablet (pharmacy)", the free encyclopedia, retrieved on May 24, 2023.
Wikipedia, "Withania somnifera", the free encyclopedia, retrieved on May 24, 2023.
Xiong et al., "Virucidal activity of Moringa A from Moringa oleifera seeds against Influenza A Viruses by regulating TFEB", International Immunopharmacology, vol. 95, Jun. 2021, 107561.

|  | Never | Sometimes | Regularly | Often | (Almost) always |
|---|---|---|---|---|---|
| Sudden high fever |  |  |  |  |  |
| Diarrhea |  |  |  |  |  |
| Headache |  |  |  |  |  |
| Skin problems (e.g acne & eczema) |  |  |  |  |  |
| Muscle and joint pain |  |  |  |  |  |
| Common Cold |  |  |  |  |  |
| Coughing |  |  |  |  |  |

FIG. 6

| | Do not have this symptom 0 | Very mild 1 | 2 | Mild 3 | 4 | Moderate 5 | 6 | Severe 7 |
|---|---|---|---|---|---|---|---|---|
| Runny nose | o | o | o | o | o | o | o | o |
| Plugged nose | o | o | o | o | o | o | o | o |
| Sneezing | o | o | o | o | o | o | o | o |
| Sore throat | o | o | o | o | o | o | o | o |
| Scratchy throat | o | o | o | o | o | o | o | o |
| Cough | o | o | o | o | o | o | o | o |
| Hoarseness | o | o | o | o | o | o | o | o |
| Head congestion | o | o | o | o | o | o | o | o |
| Chest congestion | o | o | o | o | o | o | o | o |
| Feeling tired | o | o | o | o | o | o | o | o |

FIG. 8

| | Not at all 0 | Very mildly 1 | Mildly 2 | 3 | Moderately 4 | 5 | 6 | Severely 7 |
|---|---|---|---|---|---|---|---|---|
| Think clearly | o | o | o | o | o | o | o | o |
| Sleep well | o | o | o | o | o | o | o | o |
| Breathe easily | o | o | o | o | o | o | o | o |
| Walk, climb stairs, exercise | o | o | o | o | o | o | o | o |
| Accomplish daily activities | o | o | o | o | o | o | o | o |
| Work outside the home | o | o | o | o | o | o | o | o |
| Work inside the home | o | o | o | o | o | o | o | o |
| Interact with others | o | o | o | o | o | o | o | o |
| Live your personal life | o | o | o | o | o | o | o | o |

FIG. 10

PART A- Generele Questions

|   |   | Very poor | Poor | Neither poor nor good | Good | Very good |
|---|---|---|---|---|---|---|
| 1 | How would you rate your quality of life? | 1 | 2 | 3 | 4 | 5 |
|   |   | Very dissatisfied | Dissatisfied | Neither satisfied not dissatisfied | Satisfied | Very satisfied |
| 2 | How satisfied are you with your health? | 1 | 2 | 3 | 4 | 5 |

The following questions ask about how much you have experienced certain things in the last two weeks.

|   | | Not at all | A little | A moderate amount | Very much | An extreme amount |
|---|---|---|---|---|---|---|
| 3 | To what extent do you feel that physical pain prevents you from doing what you need to do? | 1 | 2 | 3 | 4 | 5 |
| 4 | How much do you need any medical treatment to function in your daily life? | 1 | 2 | 3 | 4 | 5 |
| 5 | How much do you enjoy life? | 1 | 2 | 3 | 4 | 5 |
| 6 | To what extent do you feel your life to be meaningful? | 1 | 2 | 3 | 4 | 5 |
| 7 | How well are you able to concentrate? | 1 | 2 | 3 | 4 | 5 |
| 8 | How safe do you feel in your daily life? | 1 | 2 | 3 | 4 | 5 |
| 9 | How healthy is your physical environment? | 1 | 2 | 3 | 4 | 5 |

The following questions ask about how completely you have experienced or were able to do certain things in the last two weeks. Circle your best answer number.

| | | Not at all | A little | A moderate amount | Very much | Extremely |
|---|---|---|---|---|---|---|
| 10 | Do you have enough energy for everyday life? | 1 | 2 | 3 | 4 | 5 |
| 11 | Are you able to accept your body appearance? | 1 | 2 | 3 | 4 | 5 |
| 12 | Have you enough money to meet your needs? | 1 | 2 | 3 | 4 | 5 |
| 13 | How available to you is the information you need in your day-to-day life? | 1 | 2 | 3 | 4 | 5 |
| 14 | To what extent do you have the opportunity for leisure activities? | 1 | 2 | 3 | 4 | 5 |
| 15 | How well are you able to get around physically? | 1 | 2 | 3 | 4 | 5 |

FIG. 11(Continued)

The following questions ask about how good or satisfied you have felt about aspects of your life over the last two weeks.

| | | Very dissatisfied | Dissatisfied | Neither satisfied nor dissatisfied | Satisfied | Very satisfied |
|---|---|---|---|---|---|---|
| 16 | How satisfied are you with your sleep? | 1 | 2 | 3 | 4 | 5 |
| 17 | How satisfied are you with your ability to perform your daily living activities? | 1 | 2 | 3 | 4 | 5 |
| 18 | How satisfied are you with your capacity for work | 1 | 2 | 3 | 4 | 5 |
| 19 | How satisfied are you with yourself? | 1 | 2 | 3 | 4 | 5 |
| 20 | How satisfied are you with your personal relationships? | 1 | 2 | 3 | 4 | 5 |
| 21 | How satisfied are you with your sex life? | 1 | 2 | 3 | 4 | 5 |
| 22 | How satisfied are you with the support you get from your friends? | 1 | 2 | 3 | 4 | 5 |
| 23 | How satisfied are you with the conditions of your living place? | 1 | 2 | 3 | 4 | 5 |
| 24 | How satisfied are you with your access to health services? | 1 | 2 | 3 | 4 | 5 |
| 25 | How satisfied are you with your transport? | 1 | 2 | 3 | 4 | 5 |

FIG. 11(Continued)

The following question refers to how often you have felt or experienced certain things in the last two weeks.

| | | Never | Seldom | Quite often | Very often | Always |
|---|---|---|---|---|---|---|
| 26 | How often do you have negative feelings such as blue mood, despair, anxiety or depression? | 1 | 2 | 3 | 4 | 5 |

FIG. 11(Continued)

| Sl. No. | Subject ID | Visit No. | AE Description | Concomitant Medication | Severity | Relationship | Action for IP | Outcome | Group |
|---|---|---|---|---|---|---|---|---|---|
| 1 | RAPA008 | 4 | Constipation | Lactulose | Moderate | Not Related | No Action | Completely recovered | KaraShield™ |
| 2 | MSBA030 | 6 | Headache | - | Mild | Not Related | No Action | Completely recovered | KaraShield™ |
| 3 | KARA072 | 6 | Body Heat | - | Mild | Not Related | No Action | Completely recovered | KaraShield™ |
| 4 | CHEA076 | 4 | Diarrhoea | Loperamide 2mg | Mild | Not Related | No Action | Completely recovered | KaraShield™ |
| 5 | NANB033 | 4 | Fever | Paracetamol-500 mg | Mild | Not Related | No Action | Completely recovered | KaraShield™ |
| 6 | RBSA050 | 5 | Constipation | - | Mild | Not Related | No Action | Completely recovered | Placebo |
| 7 | TRPA084 | 5 | Acidity | Gelusil | Moderate | Not Related | No Action | Completely recovered | Placebo |
| 8 | SUNB002 | 5 | Headache | - | Mild | Not Related | No Action | Completely recovered | Placebo |
| 9 | ROHB026 | 5 | Dryness of mouth | - | Mild | Not Related | No Action | Completely recovered | Placebo |

FIG. 12

COMPOSITIONS AND METHODS FOR IMMUNE HEALTH

SUMMARY DISCLOSURE OF THE INVENTION

A composition includes *Andrographis paniculata* extract at about 20% to about 30% by weight of the total composition; *Withania somnifera* extract at about 16% to about 24% by weight of the total composition; *Moringa oleifera* extract at about 24% to about 36% by weight of the total composition; and *Ocimum sanctum* extract at about 20% to about 30% by weight of the total composition. The composition may be in the form of a capsule, a pill, or a tablet.

A method of maintaining, supporting, or improving immunity in a mammal includes administering the composition to a mammal, where the concentration of C-Reactive protein in the blood of the mammal is decreased, or the concentration of Immunoglobulin G in the blood of the mammal is increased. The mammal may be a human. The improved immunity may be to a virus or any infection. The improved immunity may be to an upper respiratory tract infection or symptoms associated with an upper respiratory tract infection. The maintained or supported immunity may be to a healthy mammal that does not have any current infection.

In embodiments, the compositions may consist of the *Andrographis paniculata* extract, the *Withania somnifera* extract, the *Moringa oleifera* extract, and the *Ocimum sanctum* extract.

In embodiments, the compositions may consist essentially of the *Andrographis paniculata* extract, the *Withania somnifera* extract, the *Moringa oleifera* extract, and the *Ocimum sanctum* extract. In this regard, basic and novel properties of the compositions may include, but are not limited to, improving immune health, improving immune health with respect to upper respiratory tract infections and viral infections in general, particularly in regard to decreasing C-reactive protein and increasing immunoglobulin G Other features and aspects will be apparent from the following detailed description, the drawings, and the claims.

BRIEF DESCRIPTION OF THE DRAWINGS

FIG. 6 shows items of immune status questionnaire (ISQ).

FIG. 8 shows items of upper respiratory symptoms of WURSS-24 Scale.

FIG. 10 shows items of functional impairments and abilities of wurss-24 scale.

FIG. 11 shows items of a WHO-QUALITY OF LIFE QUESTIONNAIRE.

FIG. 12 shows adverse events.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DISCLOSURE OF THE INVENTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

Upper respiratory tract infections (URTIs) are quite common, especially in autumn and winter. URTI is characterized by a wide array of acute illnesses affecting the upper airways, including tonsillitis, sinusitis, otitis media, pharyngitis, laryngitis, and the so-called "common cold". The symptoms of URTIs generally occur 24-72 hours after becoming infected but can continue for as long as 7-14 days. Viruses (mainly influenza virus, rhinovirus, coronavirus, parainfluenza virus, adenovirus, and respiratory syncytial virus) are significant causal agents involved in URTIs occurrence with rhinovirus accounting for a significant number of cases. Bacteria may also be the lone causal agents, but they are generally not as common in causing URTIs by themselves as viruses are. In adults, 2 or 3 URTIs may occur yearly, while in children 5 or more may occur yearly.

Common cold treatment options focus on reducing the severity of the symptoms, but up to date, there is no specific and effective pharmacological treatment. The first-line treatment for cold may include adequate hydration, rest, and the prevention of bacterial or viral spread. Antibiotics use in case of common cold, nasopharyngitis, and other non-specific URTIs may not result in an improvement since they are generally not effective against viruses, but analgesics, decongestants, and antipyretics can be effective in reducing pain and cold. Based on this background, investigating plants and herbal extracts for URTIs prevention or treatment may represent an important research area.

Herbal extracts are widely available and have gained popularity worldwide. Herbal extracts represent a growing industry today due to their role in improving immunity and building a strong immune system, which can then prevent or fight off numerous diseases and ailments, including viral infections and URTIs.

MODES FOR CARRYING OUT THE INVENTION

The inventive compositions are a novel, synergistic, blends comprising of compositions of extracts of four herbs—*Andrographis paniculata, Withania somnifera, Moringa oleifera,* and *Ocimum sanctum*.

Figure 1A:
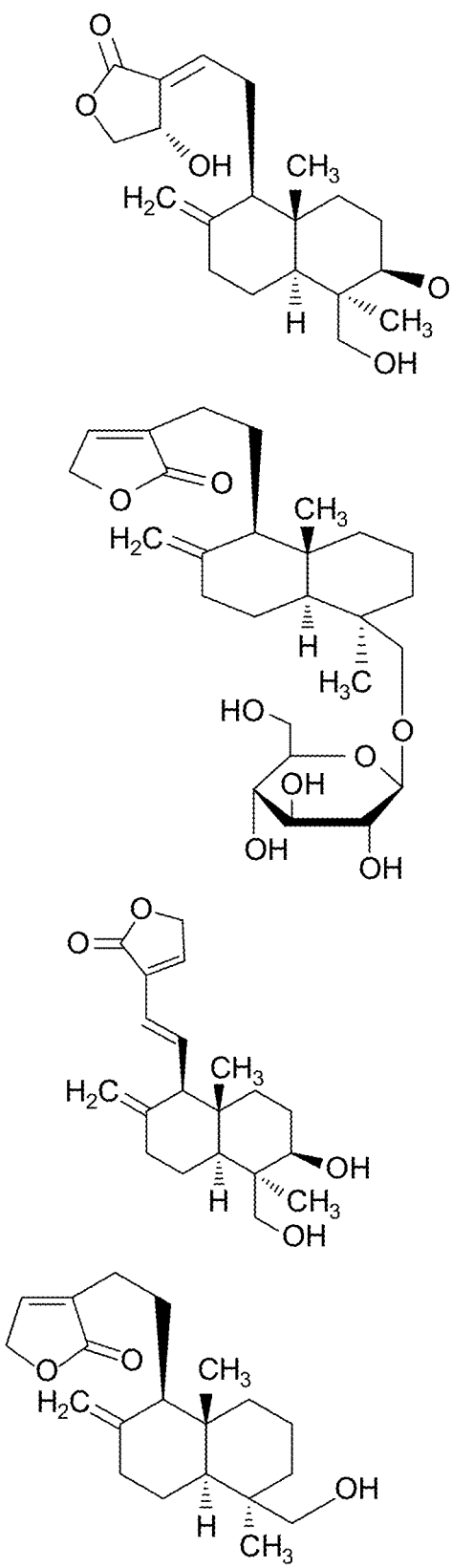
FIG. 1A shows bioactive compounds contained in *Andrographis paniculata*.

The compounds shown in FIG. 1A are major bioactive compounds that the *Andrographis paniculata* extract has been standardized to in the invention. These are basically diterpene lactones extracted from *Andrographis* paniculate including:

(3E,4S)-3-[2-[(1R,4aS,5R,6R,8aS)-6-hydroxy-5-(hydroxymethyl)-5,8a-dimethyl-2-methylidene-3,4,4a,6,7,8-hexahydro-1H-naphthalen-1-yl]ethylidene]-4-hydroxyoxolan-2-one;

4-[2-[(1R,4aS,5R,8aS)-5,8a-dimethyl-2-methylidene-5-[[(2R,3R,4S,5S,6R)-3,4,5-trihydroxy-6-(hydroxymethyl)oxan-2-yl]oxymethyl]-3,4,4a,6,7,8-hexahydro-1H-naphthalen-1-yl]ethyl]-2H-furan-5-one;

4-[(E)-2-[(1R,4aS,5R,6R,8aR)-6-hydroxy-5-(hydroxymethyl)-5,8a-dimethyl-2-methylidene-3,4,4a,6,7,8-hexahydro-1H-naphthalen-1-yl]ethenyl]-2H-furan-5-one; and 4-[2-[(1R,4aS,5R,8aS)-5-(hydroxymethyl)-5,8a-dimethyl-2-methylidene-3,4,4a,6,7,8-hexahydro-1H-naphthalen-1-yl]ethyl]-2H-furan-5-one.

Figure 1B:
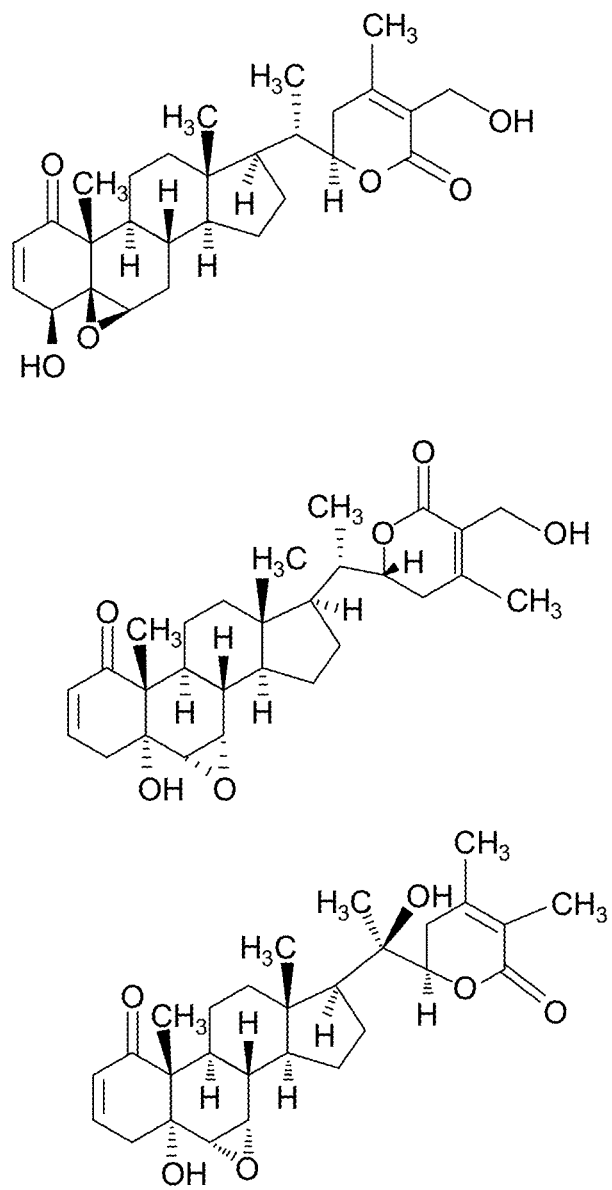
FIG. 1B shows bioactive compounds contained in *Withania somnifera* extract.

The compounds shown in FIG. 1B are major bioactive compounds that the *Withania somnifera* extract has been standardized to in the invention. The compounds include:

(1S,2R,6S,7R,9R,11S,12S,15R,16S)-6-hydroxy-15-[(1S)-1-[(2R)-5-(hydroxymethyl)-4-methyl-6-oxo-2,3-dihydropyran-2-yl]ethyl]-2,16-dimethyl-8-oxapentacyclo[9.7.0.0$^{2,7}$.0$^{7,9}$.0$^{12,16}$]octadec-4-en-3-one;

(1S,2S,4S,5R,10R,11S,14R,15R,18S)-5-hydroxy-15-[(1S)-1-[(2R)-5-(hydroxymethyl)-4-methyl-6-oxo-2,3-dihydropyran-2-yl]ethyl]-10,14-dimethyl-3-oxapentacyclo[9.7.0.0$^{2,4}$.0$^{5,10}$.0$^{14,18}$]octadec-7-en-9-one; and (1S,2S,4S,5R,10R,11S,14S,15S,18S)-15-[(1R)-1-[(2R)-4,5-dimethyl-6-oxo-2,3-dihydropyran-2-yl]-1-hydroxyethyl]-5-hydroxy-10,14-dimethyl-3-oxapentacyclo[9.7.0.0$^{2,4}$.0$^{5,10}$.0$^{14,18}$]octadec-7-en-9-one.

Figure 2:
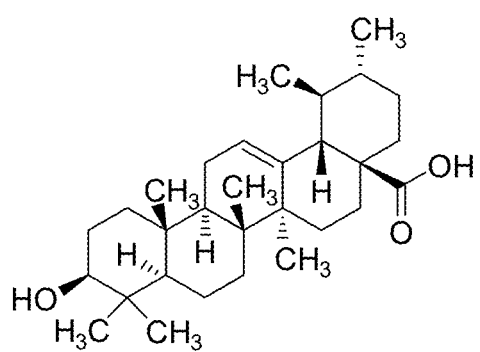
FIG. 2 shows a bioactive compound contained in *Ocimum sanctum* extract.

The compound shown in FIG. 2 is the major bioactive compound that the *Ocimum sanctum* extract has been standardized to in the invention. The compound is (1S,2R,4aS,6aR,6aS,6bR,8aR,10S,12aR,14bS)-10-hydroxy-1,2,6a,6b,9,9,12a-hepta methyl-2,3,4,5,6,6a,7,8,8a,10,11,12,13,14b-tetradecahydro-1H-picene-4a-carboxylic acid.

In embodiments, the disclosed compositions include *Andrographis paniculata* extract at about 25% by weight, *Withania somnifera* extract at about 20% by weight, *Moringa oleifera* extract at about 30% by weight, and *Ocimum sanctum* extract at about 25% by weight.

The amounts of extracts used in the disclosed compositions may vary in amounts ranging from about 1% to about 20% by weight and continue to provide compositions with a comparable level of efficacy.

Accordingly, a composition may include *Andrographis paniculata* extract at about 20% to about 30% by weight of the total composition, *Withania somnifera* extract at about 16% to about 24% by weight of the total composition, *Moringa oleifera* extract at about 24% to about 36% by weight of the total composition, and *Ocimum sanctum* extract at about 20% to about 30% by weight of the total composition.

Glossary

KaraShield™ is a blend of extracts of *Andrographis paniculata* extract, *Ocimum sanctum* extract, *Withania somnifera* extract, and *Moringa oleifera* extract. In embodiments, the composition may further include *Tinospora cordifolia* extract, *Bacopa monnieri* extract, or *Centella asiatica* extract, or combinations thereof.

C-reactive protein (CRP) is a protein found in blood plasma, whose circulating concentrations rise in response to inflammation.

Immunoglobulin G (Ig G) is a type of antibody accounting for around 75% of serum antibodies in humans. IgG binds to different pathogens and safeguards the body from infection.

The term 'therapeutically effective amount' refers to an amount of an active ingredient that produces the intended result, i.e., provides some level of treatment, modification, maintenance/support, or has an effect on immunity, viral infection, or upper respiratory tract infection in a mammal preferably a human.

The term 'administration' generally includes oral and intravenous administration as well as any route of administration capable of effectively delivering the composition to the body. Preferred would be capsules, pills, or tablets. Administration may also be done through a food or beverage or through the skin or other body cavity.

The term "therapeutically effective amount" as used herein refers to an amount of an extract, composition, or active ingredient that produces the intended (recited) result. Such amounts can be determined by routine experimentation depending on the condition and the specifics, e.g., age, weight, etc., of the individual to whom the composition is to be administered.

Dosage can be from about 100 mg to about 2000 mg per day. Preferred dosage is about 500 mg per day.

The term mammal as used herein are a group of vertebrate animals constituting the class Mammalia. Preferably mammal refers to primates and most preferably humans.

The term 'treatment' or 'treating' refers to the attempted remediation of a condition or health problem. Treatment can include providing relief to, preventing, curing, supporting, or maintaining a certain state with respect to a condition or management of a condition. Accordingly, treatment can include prevention, management, e.g., halting or slowing the condition's development and effects, and relieving the symptoms of, as well as curing or eradicating the condition.

An active ingredient or active substance in a composition is an ingredient or substance that is biologically active. In embodiments, the compositions of the disclosure can have more than one active ingredient. An active ingredient is any ingredient that provides biologically active or other direct effect in the diagnosis, cure, mitigation, treatment, or prevention of disease or to affect the structure or any function of the body of humans or animals. Excipients are generally biologically inactive ingredients, although need not necessarily be completely inert. See e.g., Active ingredient, Wikipedia, the free encyclopedia, retrieved May 24, 2023.

A tablet, capsule, or a pill is an oral dosage form that typically comprises a solid dosage with optional excipients. A tablet or a pill may also include liquids, syrups, elixirs, suspensions, and emulsions as well. See e.g., Tablet (pharmacy), Wikipedia, the free encyclopedia, retrieved May 24, 2023.

Percent amounts of extracts and active substances and other components of the claimed compositions are provided herein by weight.

The disclosed compositions may be used for maintaining/supporting or improving general immunity. The improved immunity may be to viral infections or upper respiratory tract infections, with such infections as described herein. The disclosed compositions may also be used for treating viral infections or upper respiratory tract infections, with the viral infections or upper respiratory tract infections as described herein.

*Withania somnifera*, known commonly as ashwagandha or winter cherry is an evergreen shrub in the Solanaceae or nightshade family that grows in India, the Middle East, and parts of Africa. See e.g., *Withania somnifera*, Wikipedia, the free encyclopedia, retrieved May 24, 2023.

*Ocimum sanctum*, commonly known as holy basil, tulsi or tulasi, and tamole, damole, or domole in Fiji, is an aromatic perennial plant in the family Lamiaceae. It is native to the Indian subcontinent and widespread as a cultivated plant throughout the Southeast Asian tropics. See e.g., *Ocimum tenuiflorum*, Wikipedia, the free encyclopedia, retrieved May 24, 2023. *Ocimum tenuiflorum* is a synonym for *Ocimum sanctum*.

*Andrographis paniculate*, commonly known as creat or green chiretta, is an annual herbaceous plant in the family Acanthaceae, native to India and Sri Lanka. See e.g., *Andrographis paniculata*, Wikipedia, the free encyclopedia, retrieved May 24, 2023.

*Moringa oleifera* is a fast-growing, drought-resistant tree of the family Moringaceae, native to the Indian subcontinent. Common names include *Moringa*, drumstick tree (from the long, slender, triangular seed-pods), horseradish tree (from the taste of the roots, which resembles horseradish), and ben oil tree or benzolive tree. See e.g., *Moringa oleifera*, Wikipedia, the free encyclopedia, retrieved May 24, 2023.

EXAMPLES

Example 1

Product Composition

Product name: KaraShield™: Blend of extracts of *Andrographis paniculata, Ocimum sanctum, Withania somnifera*, and *Moringa oleifera*.

| S. No | Extracts | Composition in % |
|---|---|---|
| 1. | *Andrographis paniculata* extract | 25 |
| 2. | *Withania somnifera* extract | 20 |
| 3. | *Moringa oleifera* extract | 30 |
| 4. | *Ocimum sanctum* extract | 25 |
|  | Total | 100 |

| Test parameters | Specification | Testing method |
|---|---|---|
| Physical | | |
| Appearance | Brown to greenish brown powder | Visual |
| Identification | To comply with standard | In-house - HPTLC |
| Particle size | 98% min passes through 20 mesh | USP |
| Loss on drying | NMT 5% | In-house - IR Moisture balance |
| Assay of actives | | |
| Compounds shown in FIG 1A | NLT 2.0% | Based on USP - HPLC |
| Compound shown in FIG 2 | NLT 0.2% | Based on USP - HPLC |
| Compounds shown in FIG 1B | NLT 0.3% | In-house - HPLC |
| Microbial | | |
| Total plate count | NMT 1000 cfu/g | USP |
| Yeast and mold | NMT 100 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 3 ppm | USP - ICP-MS |
| Cadmium | NMT 1 ppm | USP - ICP-MS |
| Arsenic | NMT 1 ppm | USP - ICP-MS |
| Mercury | NMT 0.1 ppm | USP - ICP-MS |
| Pesticide residues | To comply with USP limits | USP |
| Residual solvents | To comply with USP limits | USP |

*Andrographis paniculata*

Product name: *Andrographis paniculata* extract; Plant part used: Aerial parts.

Botanical name: *Andrographis paniculata* Extraction: Aqueous alcohol

Excipient used: 5% Dextrin.

| Test parameters | Specification | Testing method |
|---|---|---|
| Physical | | |
| Appearance | Greenish brown to brown powder | Visual |
| Identification (Identification using the WS of extract prepared using botanically authenticated *Andrographis paniculata* aerial parts) | To comply with standard | In-house - HPTLC |
| Particle size | 98% min passes through 20 mesh | USP |
| Loss on drying | NMT 6% | In-house - IR Moisture balance |
| Assay of actives | | |
| Compounds shown in FIG 1A | NLT 10% | USP - HPLC |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |
| *Pseudomonas aeruginosa* | Absent | USP |
| *Staphylococcus aureus* | Absent | USP |
| Chemical impurities | | |
| Lead | NMT 5 ppm | USP - ICP-MS |
| Cadmium | NMT 1 ppm | USP - ICP-MS |
| Arsenic | NMT 3 ppm | USP - ICP-MS |
| Mercury | NMT 1 ppm | USP - ICP-MS |
| Pesticide residues | To comply with USP limits | USP |
| Residual solvents | To comply with USP limits | USP |

*Withania somnifera*

Product name: *Withania somnifera* extract Plant part used: Roots containing leaves and stems; Botanical name: *Withania somnifera* Solvents used: Aqueous alcohol; Excipient used: 5% Dextrin

| Test parameters | Specification | Testing method |
|---|---|---|
| Physical | | |
| Appearance | Brown powder | Visual |
| Identification (Identification using the WS of extract prepared using botanically authenticated *Withania somnifera* roots containing leaves and stems) | To comply with standard | In-house - HPTLC |
| Particle size | 98% min passes through 20 mesh | USP |
| Loss on drying | NMT 6% | In-house - IR Moisture balance |
| Assay of actives | | |
| Compounds shown in FIG 1B | NLT 2.5% | In-house HPLC |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| *E. coli* | Absent | USP |

| Test parameters | Specification | Testing method |
|---|---|---|
| Pseudomonas aeruginosa | Absent | USP |
| Staphylococcus aureus | Absent | USP |
| Chemical impurities | | |
| Lead | NMT 5 ppm | USP - ICP-MS |
| Cadmium | NMT 1 ppm | USP - ICP-MS |
| Arsenic | NMT 3 ppm | USP - ICP-MS |
| Mercury | NMT 1 ppm | USP - ICP-MS |
| Pesticide residues | To comply with USP limits | USP |
| Residual solvents | To comply with USP limits | USP |

*Moringa oleifera*

Product name: *Moringa* leaves extract Plant part used: Leaves; Botanical name: *Moringa oleifera* Extraction: Aqueous alcohol; Excipients: 5% Dextrin

| Test parameters | Specification | Testing method |
|---|---|---|
| Physical | | |
| Appearance | Dark brown to brown powder | Visual |
| Identification (Identification using the WS of extract prepared using botanically authenticated *Moringa oleifera* leaves) | To comply with standard | In-house - HPTLC |
| Particle size | 98% min. passes through 20 mesh | USP |
| Loss on drying | NMT 6% | In-house - IR Moisture balance |
| Assay of actives | | |
| Saponins | NLT 35% | In-house - Gravimetry |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| E. coli | Absent | USP |
| Pseudomonas aeruginosa | Absent | USP |
| Staphylococcus aureus | Absent | USP |
| Chemical impurities | | |
| Lead | NMT 5 ppm | USP - ICP-MS |
| Cadmium | NMT 1 ppm | USP - ICP-MS |
| Arsenic | NMT 3 ppm | USP - ICP-MS |
| Mercury | NMT 1 ppm | USP - ICP-MS |
| Pesticide residues | To comply with USP limits | USP |

*Ocimum sanctum*

Product name: Holy basil leaves extract Plant part: Leaves; Botanical name: *Ocimum sanctum* Extraction: Aqueous alcohol; Excipients: Nil

| Test parameters | Specification | Testing method |
|---|---|---|
| Physical | | |
| Appearance | Tan to brown powder | Visual |
| Identification (Identification using the WS of extract prepared using botanically authenticated *Ocimum sanctum* leaves) | To comply with standard | In-house - HPTLC |
| Particle size | 98% min. passes through 20 mesh | USP |
| Loss on drying | NMT 6% | In-house - IR Moisture balance |
| Assay of actives | | |
| Compound Shown in FIG 2 | NLT 1.0% | USP - HPLC |
| Microbial | | |
| Total plate count | NMT 10000 cfu/g | USP |
| Yeast and mold | NMT 1000 cfu/g | USP |
| Coliforms | Absent | USP |
| Salmonella | Absent | USP |
| E. coli | Absent | USP |
| Pseudomonas aeruginosa | Absent | USP |
| Staphylococcus aureus | Absent | USP |
| Chemical impurities | | |
| Lead | NMT 5 ppm | USP - ICP-MS |
| Cadmium | NMT 1 ppm | USP - ICP-MS |
| Arsenic | NMT 3 ppm | USP - ICP-MS |
| Mercury | NMT 1 ppm | USP - ICP-MS |
| Pesticide residues | To comply with USP limits | USP |
| Residual solvents | To comply with USP limits | USP |

Example 2

Clinical Study

A randomized, parallel, double-blind, placebo-controlled clinical study for the assessment of properties of KaraShield™ to support immune health in general healthy subjects.

This clinical study is based on the Good Clinical Practices (GCP) guidelines issued by the ICH (International Conference on Harmonization of technical requirements for registration of pharmaceuticals for human use) and (Ayurvedic Unani Siddha and Homeopathic) guidelines issued by the department of AYUSH, India for the herbal and ayurvedic product's development and research in India, which is endorsed by Central Drugs Standard Control Organization (CDSCO) and supported by World Health Organization (WHO) guidelines. This study was performed in accordance with the current version of the declaration of Helsinki, in agreement with the International Conference on Harmonisation (ICH) guidelines on Good Clinical Practice (GCP), AYUSH, ICMR guidelines and other applicable rules and regulations of India.

The trial was registered prospectively with the Clinical Trials Registry, India (CTRI), hosted at the Indian Council for Medical Research's (ICMR) National Institute of Medical Statistics (NIMS) as per the mandate of Drugs Controller General, India (DCGI), the representative of the Central Drugs Standard Control Organization (CDSCO), India. The CTRI functions in association with the World Health Organization (WHO) registry platform.

INDICATION STUDIED: General Immunity in healthy subjects; TRIAL DESIGN: Randomized, Double-blind, Placebo-controlled, Parallel study; TREATMENT DURATION: 60 Days; ROUTE, DOSAGE FORM & DOSE: Oral administration, Capsules; KaraShield™: 500 mg once daily; Placebo: 500 mg once daily.

PATIENT POPULATION: 120 male and female subjects in the age range of 18 to 60 years (both age included) were recruited and equally distributed into the KaraShield™ arm and placebo arm.

Each subject was provided with a Subject Information Sheet (SIS) with detailed procedures involved in the study (aims, methodology, potential risks, and anticipated benefits) approved by the ethics committee. The Investigator explained the study to each participant and provided ample time to consider and clarify the information presented. The investigator or designee ensured that the study is appropriate for the subject. The investigator obtained the subject's written informed consent prior to any study-related procedures to indicate that the subject fully understood the information, and willingly volunteered to participate in the study. The subjects were asked if he/she understands that the study is for research purposes only and that it may not provide any therapeutic benefit to the individual. Subjects were informed they could withdraw from the study at any time for any reason and were given a copy of the informed consent form. The original copy of the informed consent was kept in confidential file at the clinical site for records. Volunteers were subjected to screening procedures after consenting process. Reasons for exclusion were documented for subjects found ineligible during the screening period.

Type/Design of Study

The proposed study was a multicentre, double-blind, placebo-controlled, two-arm, parallel study.

Study Objectives

To assess the Efficacy of 500 mg dose of KaraShield™ versus 500 mg dose of placebo in supporting immunity in healthy individuals.

To assess the Safety and tolerability of 500 mg dose of KaraShield™ versus 500 mg dose of placebo in supporting immunity in healthy individuals.

Study End Points

Change from the baseline to the end of the treatment period in the Incidence of clinically confirmed episodes of upper respiratory tract symptoms (URI) and related conditions measured by using Wisconsin Upper Respiratory Symptom Survey (WURSS-24) Score.

Change from the baseline to the end of the treatment period in:
Immunity status Questionnaire (ISQ) Score;
Mean symptoms severity score of WURSS-24 Score;
Immunoglobulin G (IgG) Level;
CD3, CD4 & CD8 Count;
WHO-Quality of Life (WHOQOL-BREF);
C-Reactive Protein (CRP).

Endpoints for Safety

Adverse events (AEs), frequency and severity.

Laboratory Safety Parameters (Complete Blood Profile-CBP), Liver Function Test (LFT)-SGOT, SGPT, GGT, ALP, Serum Albumin, Serum Bilirubin, Renal Function Test (RFT)-Serum Urea, Serum Creatinine, Uric Acid, Urine analysis (Routine), UPT (For women of child-bearing potential), HIV, HCV.

Treatment Emergent Adverse events (AEs)-frequency and severity

Changes in vital parameters.

Proportion of subjects who discontinue study treatment due to adverse events.

Figure 3:
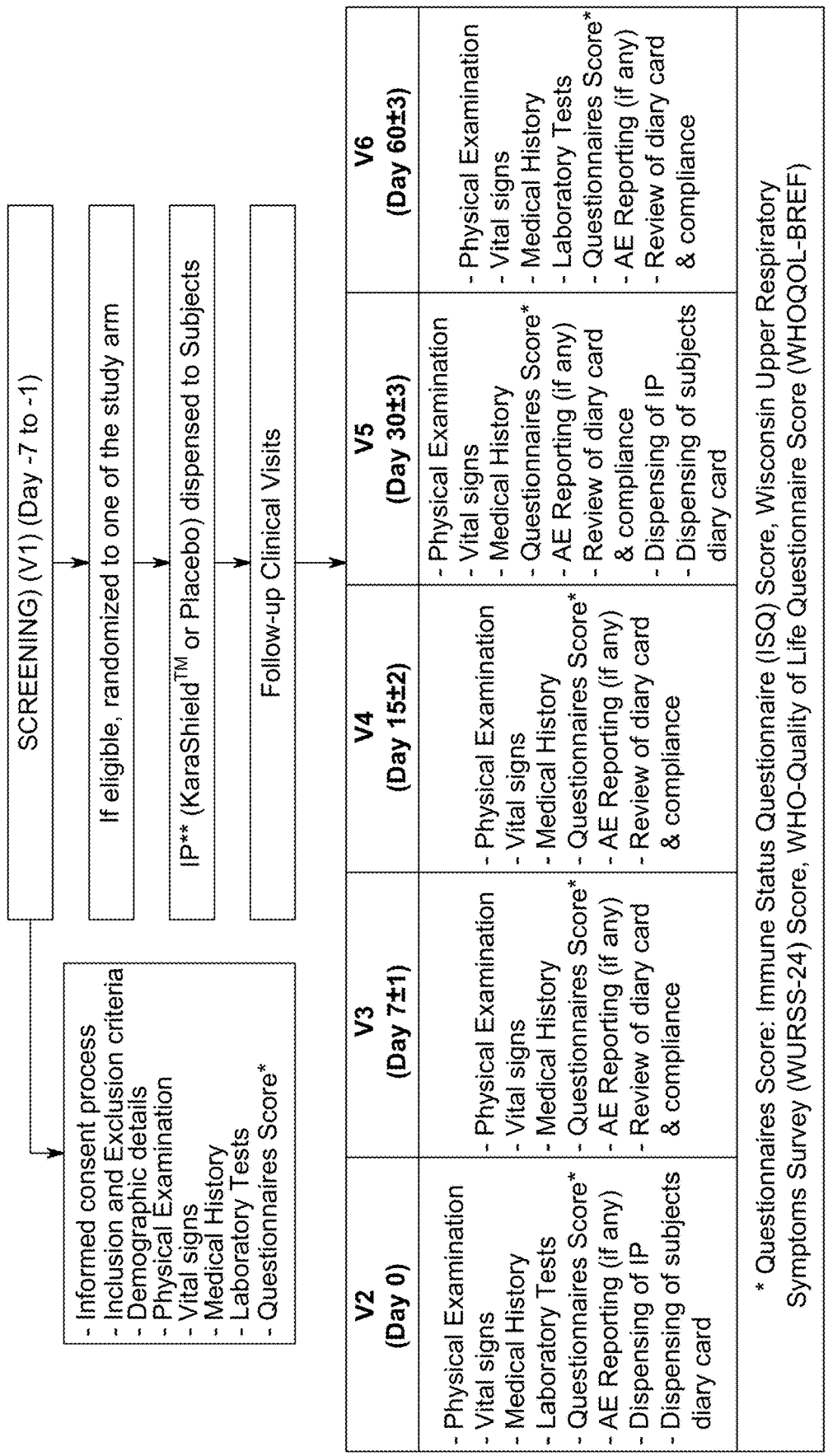
FIG. 3 shows a schematic representation of the overall clinical study design.

FIG. 3 shows a schematic representation of the overall study design.

TABLE 2

SCHEDULE OF EVENTS _KaraShield ™ STUDY

| Events | Screening Visit (V1) (Day-7 to Day-1) | Recruitment Visit (V2) (Day 0) | Follow-Up Visit (V3) (Day 7 ± 1) | Follow-Up Visit (V4) (Day 15 ± 2) | Follow-Up Visit (V5) (Day 30 ± 3) | Follow-Up Visit (V6) (Day 60 ± 3) |
|---|---|---|---|---|---|---|
| Subject ID allocation, Informed consent, Screening & Eligibility Assessment (Inclusion and Exclusion criteria) | √ | X | X | X | X | X |
| Demographics | √ | X | X | X | X | X |
| Physical Examination*, Vitals (BP, Body Temp & Pulse rate) & Medical History record | √ | √ | √ | √ | √ | √ |
| Concurrent illnesses and Concomitant medication record | √ | √ | √ | √ | √ | √ |
| Immunity status Questionnaire (ISQ) Score | √ | √ | √ | √ | √ | √ |
| Wisconsin Upper Respiratory Symptom Survey (WURSS-24) Score | √ | √ | √ | √ | √ | √ |
| WHO-Quality of Life Questionnaire Score (WHOQOL-BREF) | √ | √ | √ | √ | √ | √ |
| HIV, HBsAg & HCV Tests (Rapid card Test), IgE | √ | X | X | X | X | X |
| ** Urine Pregnancy Test (UPT) (Rapid card Test) | √ | X | X | X | √ | √ |
| Complete Blood Profile-CBP, Liver Function Test (LFT)-SGOT, SGPT, GGT, ALP, Serum Albumin, Serum Bilirubin, Renal Function Test (RFT)-Serum Urea, Serum Creatinine, Uric Acid, Urine analysis (Routine), IgG, CD3, CD4 & CD8 Count, C-Reactive Protein (CRP) | √ | X | X | X | X | √ |

TABLE 2-continued

SCHEDULE OF EVENTS KaraShield™ STUDY

| Events | Screening Visit (V1) (Day-7 to Day-1) | Recruitment Visit (V2) (Day 0) | Follow-Up Visit (V3) (Day 7 ± 1) | Follow-Up Visit (V4) (Day 15 ± 2) | Follow-Up Visit (V5) (Day 30 ± 3) | Follow-Up Visit (V6) (Day 60 ± 3) |
|---|---|---|---|---|---|---|
| Investigational Product dispensing &instructions for doses consumption & compliance | X | √ | √ | √ | √ | X |
| Subject's diary card dispensing & instructions for consumption record | X | √ | √ | √ | √ | X |
| AE Reporting | √ | √ | √ | √ | √ | √ |

*Height was measured only once at the screening visit.
** This test was done only for the female subjects of child bearing potential Recruitment, Treatment and Disposition of Subjects Nature of Research Population Healthy male and female subjects between the age groups of 18-60 years, who had a history of recurrent incidences (at least 2 episodes and above in the last 2 months) of clinically confirmed symptoms of upper respiratory tract such as common cold, cough, sore (scratchy) throat, nasal discharge (runny nose), nasal obstruction (plugged or congested), sneezing, headache, tired ness/bodyache, chillness, etc. due to common cold and/or seasonal change-related symptoms (except the allergic conditions).

Subjects Screening and Eligibility Assessments

Once the study was approved by the respective ethics committees followed by the registration of the study with at the Clinical Trial Registry, India (CTRI), the prospective subjects were invited to the centres and registered by assigning a unique identification code/Subject ID. This Subject ID was maintained throughout the study duration to serve the subjects' confidentiality. Each registered subject had undergone a formal informed consent process, which was documented on the approved version of informed consent form prior to undergoing the screening procedures of inclusion and exclusion criteria.

Inclusion Criteria

Healthy male and female subjects between the age groups of 18-60 years, who had a history of recurrent incidences (at least 2 episodes and above in the last 2 months) of clinically confirmed symptoms of upper respiratory tract such as common cold, cough, sore (scratchy) throat, nasal discharge (runny nose), nasal obstruction (plugged or congested), sneezing, headache, tiredness/bodyache, chillness, etc. due to common cold and/or seasonal change-related symptoms (except the allergic conditions).

Subjects willing to participate and comply with the protocol procedures by signing an Informed Consent Form to participate in the study.

Exclusion Criteria

Subjects with the current habit or history of cigarette smoking.

Subjects with the current habit of alcohol consumption more than 2 standard drinks/day.

Subjects with high level of IgE<700 KU/L (allergic patient)

Subjects with the confirmed case of pneumonia or bronchitis.

Subjects with allergic rhinitis, sinusitis/Pharyngitis or any other oropharyngeal disorder.

Subjects who underwent or need tonsillectomy or adenoidectomy.

Subjects with any known significant systemic disease/disorder, i.e., hepatic, renal, oesophageal, gastrointestinal, cardiovascular, psychological, neurological etc.

Subjects suffering from proteinuria (loss of protein in urine).

Subjects on any seizure medication.

Subjects on any other medication known to reduce IgG levels.

Subjects with a known history of any malignant disease.

Subjects with known history of autoimmune disease and other systemic diseases related to immune system.

Subjects with chronic immune diseases like HIV.

Subjects suffering with the infectious diseases HBsAg and HCV

Subjects treated with the following medications:
a) Antibiotics less than one week before the study
b) Any vaccination less than 4 weeks before the study
c) Concomitant immunosuppressive or immune-stimulating therapy 3 months before the study start.

Subjects with concomitant treatment with corticosteroids.

Subjects who participated in another clinical trial less than 3 months prior to this study.

Subjects who are suffering from any communicable disease.

Female subjects, who were pregnant, breast feeding or expecting pregnancy during the study period.

Subjects with the history of consumption of any recreational drugs (such as cocaine, methamphetamine, marijuana, etc.).

Subjects who were scheduled for any surgery within 3 months period of completing the study.

Subjects who were pre-diabetic/diabetic or hypertensive or hyperlipidemic

Subjects with inability or unwillingness to abide by the requirements of the protocol.

Subjects who were incompetent to sign an Informed Consent Form.

Any criteria, which in the opinion of the Investigator, suggested that the subject would not be compliant with the study protocol.

Subjects' Enrolment and Randomization Procedure

Final eligibility of the subject was ascertained through the clinical assessments and blood and urine test reports by the Investigators. A subject was confirmed as deemed eligible for enrolling into the study only when all of the inclusion criteria questions were answered "Yes" and all of the exclusion criteria questions were answered "No". A total of fourteen (14) subjects were found to be disqualified for the inclusion due to abnormal findings of biochemistry tests results (e.g., abnormal serum glucose value, abnormal parameters of liver function test, high value of IgE, and abnormal values of CRP). A total of eight (8) subjects voluntarily withdrawn themselves to participate before enrolment/randomization due to their respective personal reasons.

Each eligible subject was dispensed the capsules bottles in the sequential order as per the first come first serve basis on the scheduled randomization day. The numeric code labelled on the capsules bottle served as the unique randomization number assigned to the particular subject. The sequence of the code was strictly followed by the investigators while dispensing the capsules bottles to maintain the integrity of the randomization and blinding.

Assigning Treatment Groups and Study Arms

Eligible subjects were allocated to one of the two study arms (groups) in accordance with the randomization code mentioned on the label of the capsule's bottles.

Study Arm 1(n=60): KaraShield™ (500 mg).

Study Arm 2 (n=60): Placebo (500 mg).

Treatment Duration and Compliance

Subjects were advised to take one capsule daily after the first meal in the morning for 60±6 days. The intake of the capsules was recorded into the daily diary card issued to them on the randomization day. Missed dose, if any, was also recorded with the reason in the prescribed section of diary cards. The entries of the capsule's consumption, missed doses and left over capsules in the bottles were physically verified by the investigators and assigned site staffs to ascertain the compliance of the subjects. A total of four (4) subjects from the treatment group and five (5) from the placebo group discontinued the study due to their personal respective reasons.

Figure 4:
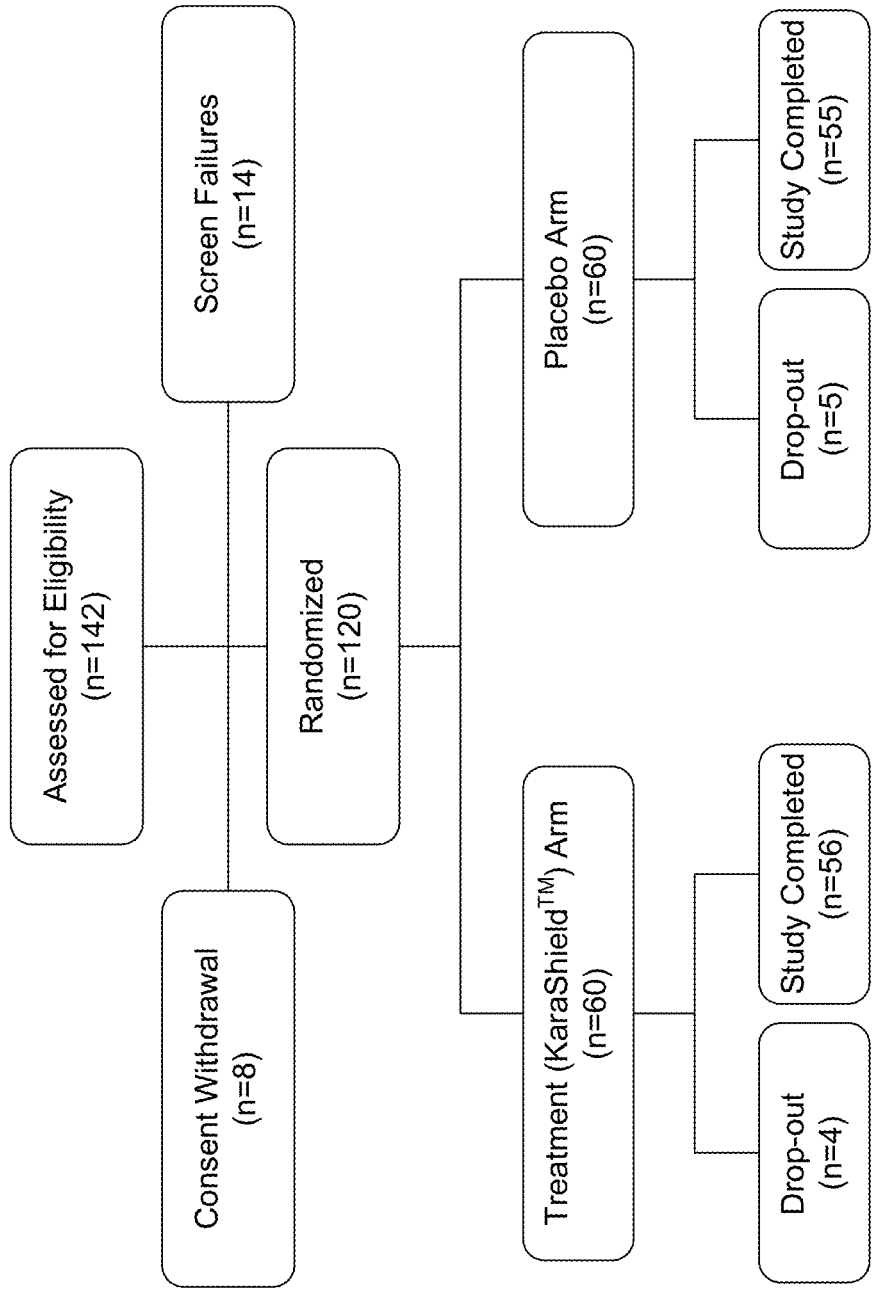
FIG. 4 shows Disposition of Subjects.

FIG. 4 shows Disposition of Subjects.

Statistical Analysis of Data

Unless otherwise stated, all hypotheses were tested at a significance level of 0.05 and 95% confidence interval.

Analysis of Baseline Assessment

Descriptive analyses for baseline summary statistics, including mean, medians and standard deviation for age, height, weight were provided by treatment group at day 0 (baseline) (V2) and compared using statistical tests appropriate for the variable under consideration.

TABLE 3(a)

STATISTICAL ANALYSIS OF DEMOGRAPHY-WEIGHT (PER PROTOCOL POPULATION)

| Variable | T Group (N = 56) | P Group (N = 55) | P value [a] |
|---|---|---|---|
| Weight (kg) at day 0 (V2) | 61.30 (4.736) | 62.25 (5.111) | 0.6149 |
| Weight (kg) at day 7 (V3) | 61.31 (4.754) | 62.25 (5.111) | |
| Mean Difference (SD) | 0.01 (0.151) | — | |
| P Value [b] | 0.6588 | — | |
| Weight (kg) at day 0 (V2) | 61.30 (4.736) | 62.25 (5.111) | 0.0505 |
| Weight (kg) at day 15 (V4) | 61.22 (4.609) | 62.31 (5.080) | |
| Mean Difference (SD) | −0.08 (0.424) | 0.06 (0.405) | |
| P Value [b] | 0.1618 | 0.3218 | |
| Weight (kg) at day 0 (V2) | 61.30 (4.736) | 62.25 (5.111) | 0.0057 |
| Weight (kg) at day 30 (V5) | 60.93 (4.455) | 62.20 (5.082) | |
| Mean Difference (SD) | −0.37 (0.906) | −0.05 (0.356) | |
| P Value [b] | 0.0031 | 0.2606 | |
| Weight (kg) at day 0 (V2) | 61.30 (4.736) | 62.25 (5.111) | 0.0744 |
| Weight (kg) at day 60 (V6) | 60.52 (4.108) | 61.76 (4.876) | |
| Mean Difference (SD) | −0.78 (1.474) | −0.49 (1.120) | |
| P Value [b] | 0.0002 | 0.0020 | |

* P Value [a]. Compared between groups; p-value for ANCOVA.
* P Value [b]. Compared Within groups; p-value for Paired t-test.

TABLE 3(b)

SUMMARY OF DEMOGRAPHY-WEIGHT (PER PROTOCOL POPULATION)

| Name | Statistics | T Group (N = 56) | P Group (N = 55) |
|---|---|---|---|
| Weight (kg) at day 0 (V2) | n | 56 | 55 |
| | Mean (SD) | 61.30 (4.736) | 62.25 (5.111) |
| | Median | 60.5 | 62.0 |
| | (Q1, Q3) | (58.00, 64.00) | (58.00, 66.00) |
| | (Min, Max) | (54.00, 74.00) | (54.00, 74.00) |
| Weight (kg) at day 7 (V3) | n | 56 | 55 |
| | Mean (SD) | 61.31 (4.754) | 62.25 (5.111) |
| | Median | 60.5 | 62.0 |
| | (Q1, Q3) | (58.00, 64.00) | (58.00, 66.00) |
| | (Min, Max) | (54.00, 74.00) | (54.00, 74.00) |
| Weight (kg) at day 15 (V4) | n | 56 | 55 |
| | Mean (SD) | 61.22 (4.609) | 62.31 (5.080) |
| | Median | 60.5 | 62.0 |
| | (Q1, Q3) | (58.00, 64.00) | (58.00, 66.00) |
| | (Min, Max) | (54.00, 74.00) | (54.00, 74.00) |
| Weight (kg) at day 30 (V5) | n | 56 | 55 |
| | Mean (SD) | 60.93 (4.455) | 62.20 (5.082) |
| | Median | 61.0 | 62.0 |
| | (Q1, Q3) | (57.00, 64.00) | (58.00, 66.00) |
| | (Min, Max) | (54.00, 72.00) | (54.00, 74.00) |
| Weight (kg) at day 60 (V6) | n | 56 | 55 |
| | Mean (SD) | 60.52 (4.108) | 61.76 (4.876) |
| | Median | 59.5 | 62.0 |
| | (Q1, Q3) | (57.00, 64.00) | (58.00, 64.00) |
| | (Min, Max) | (54.00, 71.00) | (55.00, 74.00) |

TABLE 3(c)

STATISTICAL ANALYSIS OF DEMOGRAPHY-BODY MASS INDEX (BMI) (PER PROTOCOL POPULATION)

| Variable | T Group (N = 56) | P Group (N = 55) | P value [a] |
|---|---|---|---|
| BMI (kg/m$^2$) at day 0 (V2) | 23.62 (2.906) | 23.58 (3.154) | 0.6365 |
| BMI (kg/m$^2$) at day 7 (V3) | 23.63 (2.917) | 23.58 (3.154) | |
| Mean Difference (SD) | 0.01 (0.064) | — | |
| P Value [b] | 0.6298 | — | |
| BMI (kg/m$^2$) at day 0 (V2) | 23.62 (2.906) | 23.58 (3.154) | 0.0979 |
| BMI (kg/m$^2$) at day 15 (V4) | 23.59 (2.875) | 23.61 (3.144) | |
| Mean Difference (SD) | −0.03 (0.166) | 0.02 (0.154) | |
| P Value [b] | 0.1733 | 0.3369 | |
| BMI (kg/m$^2$) at day 0 (V2) | 23.62 (2.906) | 23.58 (3.154) | 0.0201 |
| BMI (kg/m$^2$) at day 30 (V5) | 23.48 (2.848) | 23.56 (3.118) | |
| Mean Difference (SD) | −0.14 (0.347) | −0.02 (0.154) | |
| P Value [b] | 0.0032 | 0.2569 | |
| BMI (kg/m$^2$) at day 0 (V2) | 23.62 (2.906) | 23.58 (3.154) | 0.2365 |
| BMI (kg/m$^2$) at day 60 (V6) | 23.32 (2.750) | 23.40 (3.081) | |
| Mean Difference (SD) | −0.30 (0.586) | −0.18 (0.427) | |
| P Value [b] | 0.0003 | 0.0020 | |

*P Value [a]. Compared between groups; p-value for ANCOVA
*P Value [b]. Compared Within groups; p-value for Paired t-test TABLE 3(d)

SUMMARY OF DEMOGRAPHY-BODY MASS INDEX (BMI) (PER PROTOCOL POPULATION)

| Name | Statistics | T Group (N = 56) | P Group (N = 55) |
|---|---|---|---|
| BMI (kg/m$^2$) at day 0 (V2) | n | 56 | 55 |
| | Mean (SD) | 23.62 (2.906) | 23.58 (3.154) |
| | Median | 23.4 | 23.7 |
| | (Q1, Q3) | (21.53, 25.32) | (20.54, 26.49) |
| | (Min, Max) | (18.55, 31.43) | (18.56, 31.43) |
| BMI (kg/m$^2$) at day 7 (V3) | n | 56 | 55 |
| | Mean (SD) | 23.63 (2.917) | 23.58 (3.154) |
| | Median | 23.3 | 23.7 |

TABLE 3(d)-continued

SUMMARY OF DEMOGRAPHY-BODY MASS INDEX (BMI)
(PER PROTOCOL POPULATION)

| Name | Statistics | T Group (N = 56) | P Group (N = 55) |
| --- | --- | --- | --- |
| | (Q1, Q3) | (21.53, 25.32) | (20.54, 26.49) |
| | (Min, Max) | (18.55, 31.43) | (18.56, 31.43) |
| BMI (kg/m$^2$) at day 15 (V4) | n | 56 | 55 |
| | Mean (SD) | 23.59 (2.875) | 23.61 (3.144) |
| | Median | 23.3 | 23.7 |
| | (Q1, Q3) | (21.53, 25.32) | (20.54, 26.49) |
| | (Min, Max) | (18.55, 31.00) | (18.56, 31.43) |
| BMI (kg/m$^2$) at day 30 (V5) | n | 56 | 55 |
| | Mean (SD) | 23.48 (2.848) | 23.56 (3.118) |
| | Median | 22.8 | 23.7 |
| | (Q1, Q3) | (21.53, 25.24) | (20.54, 26.26) |
| | (Min, Max) | (18.55, 31.00) | (18.56, 31.43) |
| BMI (kg/m$^2$) at day 60 (V6) | n | 56 | 55 |
| | Mean (SD) | 23.32 (2.750) | 23.40 (3.081) |
| | Median | 22.9 | 23.7 |
| | (Q1, Q3) | (21.15, 24.97) | (20.54, 25.83) |
| | (Min, Max) | (18.24, 29.28) | (18.56, 31.43) |

Safety Analysis Set

The safety analysis set consists of all subjects who were included for the trial and took at least one dose of study product (Intention-to-treat (ITT)-safety analysis set). Intention-to-treat (ITT)-safety population is constituted by those for which at least a paired set of data is available, allowing evaluation versus baseline.

Efficacy Analysis Set

The Intention-to-treat (ITT) efficacy analysis set consists of all subjects who took at least one dose of study product and undergone at least one post-baseline assessment.

The missing observations was imputed using LOCF (last observation carried forward) approach. The Per-protocol (PP) analysis set is a subset of the Intention-to-treat (ITT) population, consisting of those subjects who had no major protocol deviations affecting the primary efficacy variables.

Efficacy Assessments

Primary Efficacy Parameters

Efficacy was based primarily on the change from baseline to end of the trial period in the episodes of clinically confirmed incidences of Upper Respiratory Tract symptoms (URI) and related conditions in both groups. It was measured by using the Wisconsin Upper Respiratory Symptom Survey (WURSS-24) questionnaire. Per-protocol (PP) populations were used for the primary efficacy analysis. Analysis of primary efficacy variable was based on the ANCOVA model.

Secondary Efficacy Parameters

Secondary parameter assessment was based on the change from the baseline to the end of the trial period in:

Immunity status Questionnaire (ISQ) Score;
Mean symptoms severity score of WURSS-24 Score;
Immunoglobulin G (IgG) Level;
CD3, CD4 & CD8 Count;
WHO-Quality of Life (WHOQOL-BREF);
C-Reactive Protein (CRP).

Safety Assessments

Physical Examination, Medical History and Concomitant Medication

A complete physical examination was conducted at all visits. Height was measured at screening visit only. Physical examinations included the following areas: head, eyes, ears, nose, throat, neck (including an examination of the thyroid), heart, lungs, abdomen (including an examination of the liver and spleen), lymph nodes, extremities, nervous system and skin. Vital signs (blood pressure and oral body temperature after sitting for 5 minutes) and body weight was recorded at all visits. A complete medical history was recorded during the screening period and review of concomitant medication throughout the study period at all visits. The observations were recorded appropriately in the required section of Case Report Forms (CRF).

Clinical Laboratory Tests

Each subject had undergone the clinical laboratory tests listed in table 4. Urine and blood samples were collected at the screening visit and final visit (V6).

TABLE 4

LIST OF LABORATORY TESTS

| Parameters | V1 Screening Visit (Day −7 to −1) | V6 Final Visit (Day 60 ± 3) |
| --- | --- | --- |
| Complete Blood Profile (CBP) | √ | √ |
| Liver Function Test (LFT)-SGOT, SGPT, GGT, ALP, Serum Albumin, Serum Bilirubin, Total Protein | √ | √ |
| Renal Function Test (RFT)-Serum Urea, Serum Creatinine | √ | √ |
| Uric Acid | √ | √ |
| Immunoglobulin G (IgG) | √ | √ |
| Immunoglobulin E (IgE) | √ | X |
| CD3, CD4 & CD8 Count | √ | √ |
| C-Reactive Protein (CRP) | √ | √ |
| HIV, HBsAg & HCV Tests | √ | X |
| Urine analysis (Routine) | √ | √ |
| ** Urine Pregnancy Test (UPT) | √ | √ |

** This test was done only for the female subjects of childbearing potential.

Analysis of Efficacy Parameters

Normality test was done for each variable. In case, the variable was not normal then a non-parametric method was used and in case, the variable was normal, then a parametric method was used for the analysis.

Episodes of Clinically Confirmed Incidences of Upper Respiratory Tract Symptoms and Related Conditions Incidences were referred to one or more of the symptoms associated with upper respiratory tract conditions mentioned under the WURSS-24 scale.

Episodes were referred to the number of times the subjects showed any of the clinically confirmed upper respiratory tract symptoms during the last sixty days prior to the study participation and during the treatment duration of sixty days.

The following incidences of the symptoms of upper respiratory tract conditions were considered as the standard of assessment for the selection and suitability of participants into this study: Runny nose, plugged nose, sneezing, sore throat, scratchy throat, cough, hoarseness, head congestion, chest congestion, feeling tired, headache, body aches and fever.

TABLE 5

SUMMARY OF EPISODES OF INCIDENCES
(PER PROTOCOL POPULATION)

| Name | Statistics | T Group (N = 56) | P Group (N = 55) |
| --- | --- | --- | --- |
| Episodes of incidences at day 0 (V2) | n | 56 | 55 |
| | Mean (SD) | 2.59 (0.869) | 2.18 (0.841) |
| | Median | 3.0 | 2.0 |
| | (Q1, Q3) | (2.00, 3.00) | (2.00, 3.00) |
| | (Min, Max) | (1.00, 4.00) | (1.00, 4.00) |

TABLE 5-continued

SUMMARY OF EPISODES OF INCIDENCES
(PER PROTOCOL POPULATION)

| Name | Statistics | T Group (N = 56) | P Group (N = 55) |
|---|---|---|---|
| Episodes of incidences at day 60 (V6) | n | 56 | 55 |
| | Mean (SD) | 0.48 (0.660) | 1.33 (1.233) |
| | Median | 0.0 | 1.0 |
| | (Q1, Q3) | (0.00, 1.00) | (0.00, 2.00) |
| | (Min, Max) | (0.00, 2.00) | (0.00, 4.00) |

Figure 5:
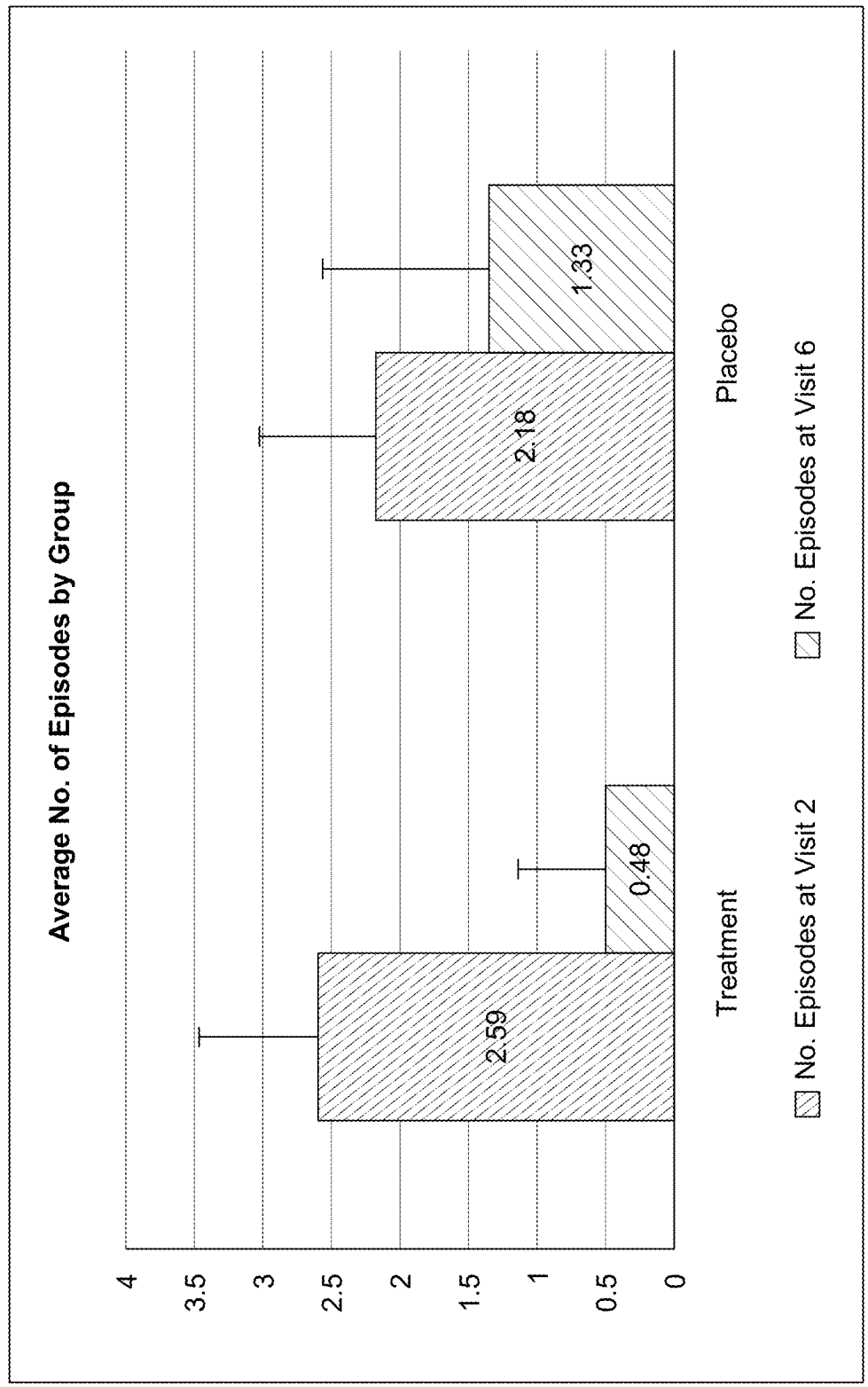
FIG. 5 shows episodes of Upper Respiratory Tract Symptoms.

FIG. 5 shows episodes of Upper Respiratory Tract Symptoms. A reduction of 81.47% in the episodes of incidences was observed in the KaraShield™ group at the end of the study period. As few of the conditions of upper respiratory tract related symptoms are self-limiting and due to psychological placebo effect, a comparatively lesser reduction of 39% in the episodes of incidences was also observed in the placebo group.

Immunity Status Questionnaire (ISQ) Score

The ISQ is a validated, short and practical scoring form and useful for clinical practice and research requiring a quick screening of the immune status of the subjects for the past twelve months. It can be used both in the clinic as for the individual as self-assessment in research surveys and screening in clinical trials. It consists of seven items related to the immune status of the body. These items are—sudden high fever, diarrhea, headache, skin problems (e.g., acne and eczema), muscle and joint pain, common cold and coughing.

FIG. 6 shows items of immune status questionnaire (ISQ). Each of the ISQ items can be scored as follows: Never=0 points; Sometimes=1 point; Regularly=2 points; Often=3 points; (Almost) always=4 points. In the ISQ raw scores interpretation, it was considered that the lower the total score higher is the immune fitness of the subject and vice versa.

TABLE 6

STATISTICAL ANALYSIS OF ISQ SCORE
(PER PROTOCOL POPULATION)

| Variable | T Group (N = 56) | P Group (N = 55) | P value[a] |
|---|---|---|---|
| ISQ at day 0 (V2) | 9.14 (2.315) | 9.00 (2.073) | 0.1869 |
| ISQ at day 7 (V3) | 8.91 (2.201) | 9.16 (2.132) | |
| Mean Difference (SD) | −0.23 (0.786) | 0.16 (2.315) | |
| P Value[b] | 0.0625 | 0.4670 | |
| % Increase/Decrease of score | −2.5% | 1.8% | |
| ISQ at day 0 (V2) | 9.14 (2.315) | 9.00 (2.073) | 0.0081 |
| ISQ at day 15 (V4) | 7.43 (2.053) | 8.58 (2.299) | |
| Mean Difference (SD) | −1.71 (2.661) | −0.42 (2.910) | |
| P Value[b] | <0.0001 | 0.3952 | |
| % Increase/Decrease of score | −18.7% | −4.7% | |
| ISQ at day 0 (V2) | 9.14 (2.315) | 9.00 (2.073) | 0.0051 |
| ISQ at day 30 (V5) | 6.88 (2.072) | 8.29 (2.283) | |
| Mean Difference (SD) | −2.27 (3.344) | −0.71 (3.236) | |
| P Value[b] | <0.0001 | 0.1144 | |
| % Increase/Decrease of score | −24.7% | −7.9% | |
| ISQ at day 0 (V2) | 9.14 (2.315) | 9.00 (2.073) | <0.0001 |
| ISQ at day 60 (V6) | 4.25 (2.510) | 8.18 (2.503) | |
| Mean Difference (SD) | −4.89 (3.489) | −0.82 (3.109) | |

TABLE 6-continued

STATISTICAL ANALYSIS OF ISQ SCORE
(PER PROTOCOL POPULATION)

| Variable | T Group (N = 56) | P Group (N = 55) | P value[a] |
|---|---|---|---|
| P Value[b] | <0.0001 | 0.0433 | |
| % Increase/Decrease of score | −53.5% | −9.1% | |

P Value[a] Compared between groups; p-value or ANCOVA or Ranked ANCOVA.

P Value[b] Compared Within groups; p-value for paired t-test or Wilcoxon signed-rank test.

TABLE 7

SUMMARY OF ISQ SCORE (PER PROTOCOL POPULATION)

| Name | Statistics | T Group (N = 56) | P Group (N = 55) |
|---|---|---|---|
| ISQ Raw Score at day 0 (V2) | n | 56 | 55 |
| | Mean (SD) | 9.14 (2.315) | 9.00 (2.073) |
| | Median | 10.0 | 8.0 |
| | (Q1, Q3) | (8.00, 12.00) | (8.00, 10.00) |
| | (Min, Max) | (6.00, 14.00) | (6.00, 12.00) |
| ISQ Raw Score at day 7 (V3) | n | 56 | 55 |
| | Mean (SD) | 8.91 (2.201) | 9.16 (2.132) |
| | Median | 8.0 | 10.0 |
| | (Q1, Q3) | (7.50, 10.00) | (8.00, 12.00) |
| | (Min, Max) | (6.00, 12.00) | (6.00, 12.00) |
| ISQ Raw Score at day 15 (V4) | n | 56 | 55 |
| | Mean (SD) | 7.43 (2.053) | 8.58 (2.299) |
| | Median | 8.0 | 8.0 |
| | (Q1, Q3) | (6.00, 8.00) | (6.00, 10.00) |
| | (Min, Max) | (4.00, 12.00) | (6.00, 12.00) |
| ISQ Raw Score at day 30 (V5) | n | 56 | 55 |
| | Mean (SD) | 6.88 (2.072) | 8.29 (2.283) |
| | Median | 6.0 | 8.0 |
| | (Q1, Q3) | (6.00, 8.00) | (6.00, 10.00) |
| | (Min, Max) | (2.00, 12.00) | (4.00, 12.00) |
| ISQ Raw Score at day 60 (V6) | n | 56 | 55 |
| | Mean (SD) | 4.25 (2.510) | 8.18 (2.503) |
| | Median | 4.0 | 8.0 |
| | (Q1, Q3) | (2.00, 6.00) | (6.00, 10.00) |
| | (Min, Max) | (0.00, 10.00) | (1.00, 12.00) |

Figure 7:
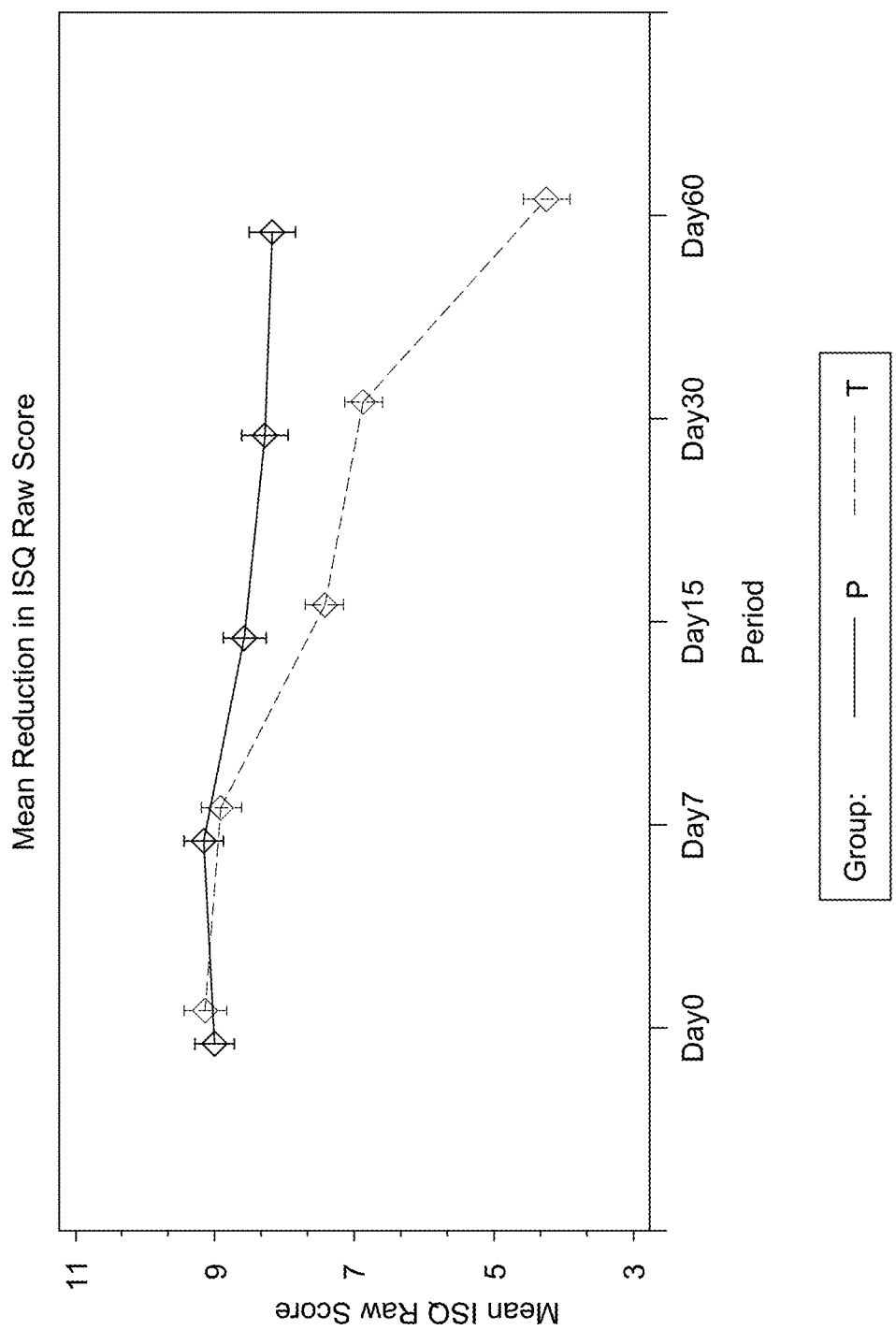
FIG. 7 shows Mean ISQ Raw Score.

FIG. 7 shows Mean ISQ Raw Score. A significant reduction (4.89 units=53.5%) (p value=<0.0001) in the mean score of Immune Status Questionnaire (ISQ) from the baseline to the end of the treatment was observed in the KaraShield™ treatment group, whereas a very minimal reduction (0.82 units=9.1%, p-value 0.0433) was observed in the placebo group. There was a difference between the groups after adjusting baseline score (ANCOVA P value<=0.0001), which implies the treatment group showed a statistically significant outperformance compared to the placebo group.

Wisconsin Upper Respiratory Symptom Survey (WURSS-24)

The Wisconsin Upper Respiratory Symptom Survey (WURSS) is a patient-oriented questionnaire instrument to assess the negative impact of acute upper respiratory conditions (URTIs) related to viral or seasonal common cold.

Wisconsin Upper Respiratory Symptom Survey (WURSS-24) Symptoms Score

The WURSS-24 includes 10 items assessing symptoms of upper respiratory tract conditions. For each parameter of symptoms, the individual score ranges from 0 (=no symptom) to 7 (=severe condition). The baseline value of the sum of the score was assessed against the sum of the score at the end of the study to see the effectiveness of the treatment during the clinical trial. The reduction in the total symptoms score is referred to as the improvement in the general health of the participants and vice versa. FIG. 8 shows items of upper respiratory symptoms of WURSS-24 Scale.

symptoms of upper respiratory tract conditions are self-limiting in nature, a little reduction in the mean symptoms score was also observed in the placebo group, but this improvement is much lower to that of the treatment group.

TABLE 8

STATISTICAL ANALYSIS OF WURSS-24 SYMPTOMS SCORE (PER PROTOCOL POPULATION)

| Variable | | T Group (N = 56) | P Group (N = 55) | P value[a] |
|---|---|---|---|---|
| WURSS-24_SYMPTOMS SCORE | Symptoms Score at day 0 (V2) | 25.27 (4.852) | 24.80 (5.222) | 0.0078 |
| | Symptoms Score at day 7 (V3) | 19.55 (6.859) | 23.22 (5.290) | |
| | Mean Difference (SD) | −5.72 (8.508) | −1.58 (7.692) | |
| | P Value[b] | <0.0001 | 0.1196 | |
| | % Increase/Decrease of score | −22.6% | −6.4% | |
| | Symptoms Score at day 0 (V2) | 25.27 (4.852) | 24.80 (5.222) | <0.0001 |
| | Symptoms Score at day 15 (V4) | 15.43 (8.358) | 22.82 (6.222) | |
| | Mean Difference (SD) | −9.84 (10.418) | −1.98 (7.304) | |
| | P Value[b] | <0.0001 | 0.0487 | |
| | % Increase/Decrease of score | −38.9% | −8.0% | |
| | Symptoms Score at day 0 (V2) | 25.27 (4.852) | 24.80 (5.222) | <0.0001 |
| | Symptoms Score at day 30 (V5) | 10.63 (8.709) | 20.47 (6.861) | |
| | Mean Difference (SD) | −14.63 (9.730) | −4.33 (9.041) | |
| | P Value[b] | <0.0001 | 0.0006 | |
| | % Increase/Decrease of score | −57.9% | −17.5% | |
| | Symptoms Score at day 0 (V2) | 25.27 (4.852) | 24.80 (5.222) | <0.0001 |
| | Symptoms Score at day 60 (V6) | 4.41 (6.519) | 16.24 (6.426) | |
| | Mean Difference (SD) | −20.86 (7.631) | −8.56 (8.569) | |
| | P Value[b] | <0.0001 | <0.0001 | |
| | % Increase/Decrease of score | −82.5% | −34.5% | |

P Value[a] Compared between groups; p-value for ANCOVA or Ranked ANCOVA.

P Value[b] Compared Within groups; p-value for paired t-test or Wilcoxon signed-rank test.

Wisconsin Upper Respiratory Symptom Survey (WURSS-24)—Functional Impairments and Abilities Score The WURSS-24 includes 9 items assessing functional impairments and abilities of participants. For each parameter

TABLE 9

SUMMARY OF WURSS-24 SYMPTOMS SCORE (PER PROTOCOL POPULATION)

| Name | | Statistics | T Group (N = 56) | P Group (N = 55) |
|---|---|---|---|---|
| WURSS-24_SYMPTOMS SCORE | Symptom Score at day 0 (V2) | n | 56 | 55 |
| | | Mean (SD) | 25.27 (4.852) | 24.80 (5.222) |
| | | Median | 25.0 | 24.0 |
| | | (Q1, Q3) | (21.00, 30.00) | (20.00, 30.00) |
| | | (Min, Max) | (18.00, 34.00) | (18.00, 34.00) |
| | Symptom Score at day 7 (V3) | n | 56 | 55 |
| | | Mean (SD) | 19.55 (6.859) | 23.22 (5.290) |
| | | Median | 20.5 | 22.0 |
| | | (Q1, Q3) | (18.00, 24.00) | (19.00, 26.00) |
| | | (Min, Max) | (6.00, 34.00) | (6.00, 34.00) |
| | Symptom Score at day 15 (V4) | n | 56 | 55 |
| | | Mean (SD) | 15.43 (8.358) | 22.82 (6.222) |
| | | Median | 18.0 | 21.0 |
| | | (Q1, Q3) | (8.00, 22.00) | (18.00, 26.00) |
| | | (Min, Max) | (1.00, 30.00) | (3.00, 34.00) |
| | Symptom Score at day 30 (V5) | n | 56 | 55 |
| | | Mean (SD) | 10.63 (8.709) | 20.47 (6.861) |
| | | Median | 8.0 | 21.0 |
| | | (Q1, Q3) | (3.00, 20.00) | (18.00, 24.00) |
| | | (Min, Max) | (1.00, 28.00) | (3.00, 34.00) |
| | Symptom Score at day 60 (V6) | n | 56 | 55 |
| | | Mean (SD) | 4.41 (6.519) | 16.24 (6.426) |
| | | Median | 1.0 | 18.0 |
| | | (Q1, Q3) | (1.00, 6.00) | (10.00, 21.00) |
| | | (Min, Max) | (0.00, 22.00) | (2.00, 30.00) |

Figure 9:
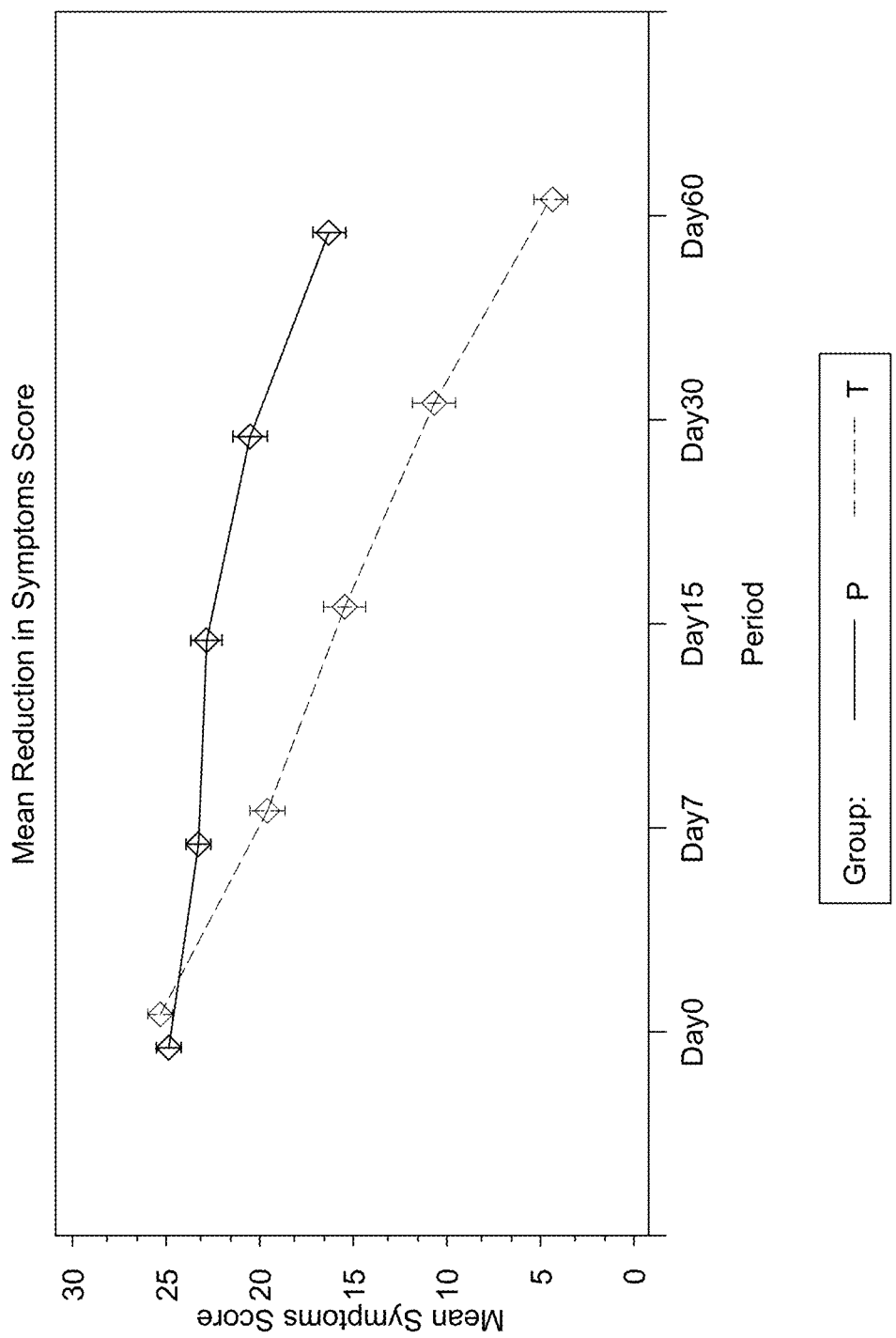
FIG. 9 shows mean symptoms score of wurss-24 scale.

FIG. 9 shows mean symptoms score of wurss-24 scale. An improvement through the statistically significant reduction in the mean symptoms score of upper respiratory tract and related conditions was prominently observed throughout the study duration in the KaraShield™ group. Since few of the of symptoms, the individual score ranges from 0 (=no symptom) to 7 (=severe condition). The baseline value of the sum of the score was assessed against the sum of the score at the end of the study to see the effectiveness of the treatment during the clinical trial. The reduction in the total symptoms score is referred to as the improvement in the functional impairments and ability of the participants and vice versa. FIG. 10 shows items of functional impairments and abilities of wurss-24 scale.

TABLE 10

STATISTICAL ANALYSIS OF WURSS-24 FUNCTIONAL IMPAIRMENTS AND ABILITIES SCORE (PER PROTOCOL POPULATION)

| | Variable | T Group (N = 56) | P Group (N = 55) | P value[a] |
|---|---|---|---|---|
| WURSS-24_FUNCTIONAL IMPAIRMENTS AND ABILITIES SCORE | Functional Ability Score at day 0 (V2) | 17.93 (7.027) | 15.64 (8.801) | 0.5914 |
| | Functional Ability Score at day 7 (V3) | 14.54 (7.515) | 15.00 (8.739) | |
| | Mean Difference (SD) | −3.39 (7.972) | −0.64 (11.441) | |
| | P Value[b] | 0.0007 | 0.6141 | |
| | % Increase/Decrease of score | −18.9% | −4.1% | |
| | Functional Ability Score at day 0 (V2) | 17.93 (7.027) | 15.64 (8.801) | 0.5873 |
| | Functional Ability Score at day 15 (V4) | 13.70 (7.368) | 14.05 (8.693) | |
| | Mean Difference (SD) | −4.23 (8.303) | −1.59 (10.979) | |
| | P Value[b] | 0.0002 | 0.1884 | |
| | % Increase/Decrease of score | −23.6% | −10.2% | |
| | Functional Ability Score at day 0 (V2) | 17.93 (7.027) | 15.64 (8.801) | 0.6244 |
| | Functional Ability Score at day 30 (V5) | 11.59 (6.909) | 12.27 (8.412) | |
| | Mean Difference (SD) | −6.34 (8.069) | −3.37 (10.303) | |
| | P Value[b] | <0.0001 | 0.0202 | |
| | % Increase/Decrease of score | −35.4% | −21.5% | |
| | Functional Ability Score at day 0 (V2) | 17.93 (7.027) | 15.64 (8.801) | 0.0091 |
| | Functional Ability Score at day 60 (V6) | 7.02 (5.355) | 10.42 (7.642) | |
| | Mean Difference (SD) | −10.91 (7.923) | −5.22 (10.217) | |
| | P Value[b] | <0.0001 | 0.0002 | |
| | % Increase/Decrease of score | −60.8% | −33.4% | |

P Value[a]. Compared between groups; p-value for ANCOVA or Ranked ANCOVA.
P Value[b]. Compared Within groups; p-value for paired t-test or Wilcoxon signed-rank test.

implies that the treatment showed better results in improving the functional abilities of the participants during the sixty days of the treatment when compared to that of the placebo. Since, the participants were otherwise healthy and were instructed to follow a healthy diet, light exercise and a good daily routine during the study, the reduction in the mean functional ability scores in both the groups can be correlated with the considerations of these associated factors as well.

TABLE 11

SUMMARY OF WURSS-24 FUNCTIONAL IMPAIRMENTS AND ABILITIES SCORE (PER PROTOCOL POPULATION)

| | Name | Statistics | T Group (N = 56) | P Group (N = 55) |
|---|---|---|---|---|
| WURSS-24_FUNCTIONAL IMPAIRMENTS AND ABILITIES SCORE | Functional Ability Score at day 0 (V2) | n | 56 | 55 |
| | | Mean (SD) | 17.93 (7.027) | 15.64 (8.801) |
| | | Median | 19.5 | 18.0 |
| | | (Q1, Q3) | (10.00, 23.00) | (6.00, 21.00) |
| | | (Min, Max) | (3.00, 32.00) | (2.00, 34.00) |
| | Functional Ability Score at day 7 (V3) | n | 56 | 55 |
| | | Mean (SD) | 14.54 (7.515) | 15.00 (8.739) |
| | | Median | 16.0 | 18.0 |
| | | (Q1, Q3) | (8.00, 21.00) | (6.00, 21.00) |
| | | (Min, Max) | (2.00, 32.00) | (2.00, 32.00) |
| | Functional Ability Score at day 15 (V4) | n | 56 | 55 |
| | | Mean (SD) | 13.70 (7.368) | 14.05 (8.693) |
| | | Median | 10.0 | 12.0 |
| | | (Q1, Q3) | (7.50, 21.00) | (6.00, 21.00) |
| | | (Min, Max) | (2.00, 26.00) | (2.00, 30.00) |
| | Functional Ability Score at day 30 (V5) | n | 56 | 55 |
| | | Mean (SD) | 11.59 (6.909) | 12.27 (8.412) |
| | | Median | 10.0 | 10.0 |
| | | (Q1, Q3) | (6.00, 17.50) | (4.00, 21.00) |
| | | (Min, Max) | (2.00, 24.00) | (2.00, 30.00) |
| | Functional Ability Score at day 60 (V6) | n | 56 | 55 |
| | | Mean (SD) | 7.02 (5.355) | 10.42 (7.642) |
| | | Median | 6.0 | 8.0 |
| | | (Q1, Q3) | (3.00, 10.00) | (4.00, 18.00) |
| | | (Min, Max) | (0.00, 22.00) | (2.00, 28.00) |

The treatment group showed better results with a reduction of 10.91 units (=60.8%, p-value<0.0001) when compared to that of the placebo group with a reduction of 5.22 units (=33.4%, p-value 0.0002) at the end of the study. This Wisconsin Upper Respiratory Symptom Survey (WURSS-24)—Global Severity and Global Change Score The WURSS-24 includes 1 item assessing global severity and global change related to the upper respiratory tract conditions and related symptoms. The scoring refers to the subjects' own assessments and reporting of the status of health. The score ranges from 1 (=Very much better) to 2 (somewhat better); 3 (A little better); 4 (The same); 5 (A little worse); 6 (Somewhat worse); and 7 (=Very much worse). A decrease in the score implies an improvement in the patient's health.

The treatment group showed better results (35% reduction, p-value<0.0001) in maintaining the general health conditions of the participants when compared to that of the placebo group (0.6%, p-value 0.9955). There was a statistically significant difference between the groups at the end of the study (P<0.0001) after adjusting the baseline score. This

TABLE 12

STATISTICAL ANALYSIS OF WURSS-24 GLOBAL SEVERITY AND GLOBAL CHANGE SCORE (PER PROTOCOL POPULATION)

| | Variable | T Group (N = 56) | P Group (N = 55) | P value[a] |
|---|---|---|---|---|
| WURSS-24_GLOBAL SEVERITY | Global Severity Score at day 0 (V2) | 3.39 (1.626) | 3.42 (1.548) | 0.6621 |
| | Global Severity Score at day 7 (V3) | 3.13 (1.237) | 3.31 (1.426) | |
| | Mean Difference (SD) | −0.26 (1.408) | −0.11 (1.931) | |
| | P Value[b] | 0.1856 | 0.6759 | |
| | % Increase/Decrease of score | −7.7% | −3.2% | |
| | Global Severity Score at day 0 (V2) | 3.39 (1.626) | 3.42 (1.548) | 0.0319 |
| | Global Severity Score at day 15 (V4) | 2.93 (1.386) | 3.47 (1.289) | |
| | Mean Difference (SD) | −0.46 (1.981) | 0.05 (1.938) | |
| | P Value[b] | 0.0518 | 0.7756 | |
| | % Increase/Decrease of score | −13.6% | 1.5% | |
| | Global Severity Score at day 0 (V2) | 3.39 (1.626) | 3.42 (1.548) | 0.0016 |
| | Global Severity Score at day 30 (V5) | 2.41 (1.411) | 3.42 (1.524) | |
| | Mean Difference (SD) | −0.98 (2.292) | 0 (1.953) | |
| | P Value[b] | 0.0028 | 0.9641 | |
| | % Increase/Decrease of score | −28.9% | 0.0% | |
| | Global Severity Score at day 0 (V2) | 3.39 (1.626) | 3.42 (1.548) | <0.0001 |
| | Global Severity Score at day 60 (V6) | 2.20 (1.341) | 3.44 (1.398) | |
| | Mean Difference (SD) | −1.19 (1.873) | 0.02 (2.014) | |
| | P Value[b] | <0.0001 | 0.9955 | |
| | % Increase/Decrease of score | −35.1% | 0.6% | |

P Value[a]: Compared between groups; p-value for ANCOVA or Ranked ANCOVA.

P Value[b]. Compared Within groups; p-value for paired t-test or Wilcoxon signed-rank test.

implies that the treatment (KaraShield™) has performed better in maintaining the general health conditions related to upper respiratory tract symptoms in the subjects during the study period of sixty days.

TABLE 13

SUMMARY OF WURSS-24 GLOBAL SEVERITY AND GLOBAL CHANGE SCORE (PER PROTOCOL POPULATION)

| | Name | Statistics | T Group (N = 56) | P Group (N = 55) |
|---|---|---|---|---|
| WURSS-24_GLOBAL SEVERITY AND GLOBAL CHANGE SCORE | Global Severity Score at day 0 (V2) | n | 56 | 55 |
| | | Mean (SD) | 3.39 (1.626) | 3.42 (1.548) |
| | | Median | 3.0 | 3.0 |
| | | (Q1, Q3) | (2.00, 5.00) | (2.00, 4.00) |
| | | (Min, Max) | (1.00, 7.00) | (1.00, 7.00) |
| | Global Severity Score at day 7 (V3) | n | 56 | 55 |
| | | Mean (SD) | 3.13 (1.237) | 3.31 (1.426) |
| | | Median | 3.0 | 3.0 |
| | | (Q1, Q3) | (2.00, 4.00) | (2.00, 4.00) |
| | | (Min, Max) | (1.00, 5.00) | (1.00, 7.00) |
| | Global Severity Score at day 15 (V4) | n | 56 | 55 |
| | | Mean (SD) | 2.93 (1.386) | 3.47 (1.289) |
| | | Median | 3.0 | 4.0 |
| | | (Q1, Q3) | (2.00, 4.00) | (2.00, 4.00) |
| | | (Min, Max) | (1.00, 6.00) | (1.00, 6.00) |
| | Global Severity Score at day 30 (V5) | n | 56 | 55 |
| | | Mean (SD) | 2.41 (1.411) | 3.42 (1.524) |
| | | Median | 2.0 | 4.0 |
| | | (Q1, Q3) | (1.00, 4.00) | (2.00, 4.00) |
| | | (Min, Max) | (0.00, 5.00) | (1.00, 7.00) |
| | Global Severity Score at day 60 (V6) | n | 56 | 55 |
| | | Mean (SD) | 2.20 (1.341) | 3.44 (1.398) |
| | | Median | 2.0 | 4.0 |
| | | (Q1, Q3) | (1.00, 3.00) | (2.00, 4.00) |
| | | (Min, Max) | (0.00, 5.00) | (0.00, 6.00) |

Immunoglobulin-G (Igg) Level in the Serum

Immunoglobulin G (Ig G) is a type of antibody accounting for around 75% of serum antibodies in humans. IgG binds to different pathogens and safeguards the body from infection.

TABLE 14

STATISTICAL ANALYSIS OF IgG LEVEL IN THE SERUM (PER PROTOCOL POPULATION)

| Variable | T Group (N = 56) | P Group (N = 55) | P value[a] |
|---|---|---|---|
| IgG (g/L) at day 0 (V2) | 12.33 (1.688) | 12.90 (2.164) | <0.0001 |
| IgG (g/L) at day 60 (V6) | 13.85 (1.843) | 12.30 (2.334) | |
| Mean Difference (SD) | 1.52 (2.316) | -0.60 (2.175) | |
| P Value[b] | <0.0001 (P) | 0.0471 (P) | |
| % Increase/Decrease | 12.3% | -4.7% | |

P Value[a]. Compared between groups; p-value for ANCOVA or Ranked ANCOVA.

P Value[b]. Compared Within groups; p-value for paired t-test or Wilcoxon signed-rank test.

Overall, an increment of 12.3% in the treatment group and a reduction of 4.7% in the placebo group were observed in the serum IgG level. The IgG value was also found to be statistically significant between the groups over the period (p value<0.0001). Within group analysis showed a statistically significant difference (improvement) in the treatment group (P<0.0001) from day 0 to day 60. Placebo showed a significant reduction within the group from day 0 to day 60 (p value=0.0471).

The treatment of KaraShield™ showed better results in managing and improving the IgG levels under the normal ranges in healthy subjects in the condition of upper respiratory symptoms. This implies that the treatment of KaraShield™ supported a better increase of immunoglobulins G (IgG) in the serum and provided good immunity to the participants when compared to that of the placebo.

CD3, CD4 & CD8 Count

CD3 (T Cells), CD4 (T helper/inducer Cells) and CD8 (T Suppressor/Cytotoxic Cells) are represented by T-Cells lymphocytes. Usually, CD3 and CD4/CD8 are the standard biomarkers panel which is commonly tested for the immunodeficiency in patients as well as to check the immunity status of an individual in case of chronic viral infections.

TABLE 16

STATISTICAL ANALYSIS OF CD3, CD4 & CD8 LEVEL IN THE SERUM (PER PROTOCOL POPULATION)

| | Variable | T Group (N = 56) | P Group (N = 55) | P value[a] |
|---|---|---|---|---|
| CD3 | CD3 (/uL) at day 0 (V2) | 1816 (433.5) | 1874 (586.2) | 0.5261 |
| | CD3 (/uL) at day 60 (V6) | 1863 (427.1) | 1829 (488.5) | |
| | Mean Difference (SD) | -47 | 45 | |
| | P Value[b] | 0.5060 (P) | 0.5730 (P) | |
| | % Increase/Decrease | 2.6% | -2.4% | |
| CD4 | CD4 (/uL) at day 0 (V2) | 1158 (485.1) | 1162 (433.0) | 0.8418 |
| | CD4 (/uL) at day 60 (V6) | 1128 (398.2) | 1142 (359.1) | |
| | Mean Difference (SD) | -30 (420.84) | -20 (373.616) | |
| | P Value[b] | 0.6032 (P) | 0.6927 (P) | |
| | % Increase/Decrease | -2.6% | -1.7% | |
| CD8 | CD8 (/uL) at day 0 (V2) | 711.6 (340.7) | 744.8 (325.9) | 0.9178 |
| | CD8 (/uL) at day 60 (V6) | 674.3 (256.2) | 704.7 (275.8) | |
| | Mean Difference (SD) | -37.3 (355.047) | -40.1 (302.443) | |
| | P Value[b] | 0.9263 | 0.4737 | |
| | % Increase/Decrease | -5.2% | -5.4% | |

TABLE 15

SUMMARY OF IgG LEVEL IN THE SERUM (PER PROTOCOL POPULATION)

| Name | Statistics | T Group (N = 56) | P Group (N = 55) |
|---|---|---|---|
| IgG (g/L) at day 0 (V2) | n | 56 | 55 |
| | Mean (SD) | 12.33 (1.688) | 12.90 (2.164) |
| | Median | 12.2 | 12.8 |
| | (Q1, Q3) | (11.20, 13.30) | (11.20, 13.90) |
| | (Min, Max) | (8.90, 16.50) | (9.60, 21.20) |
| IgG (g/L) at day 60 (V6) | n | 56 | 55 |
| | Mean (SD) | 13.85 (1.843) | 12.30 (2.334) |
| | Median | 14.0 | 12.2 |
| | (Q1, Q3) | (13.00, 15.30) | (10.30, 14.30) |
| | (Min, Max) | (9.02, 16.80) | (7.88, 16.60) |

P Value[a]. Compared between groups; p-value for ANCOVA or Ranked ANCOVA.

P Value[b]. Compared Within groups; p-value for paired t-test or Wilcoxon signed-rank test.

There was no statistically significant change in the CD3, CD4 CD8 values for either the treatment group or the placebo group.

C-Reactive Protein (Crp)

C-Reactive protein (CRP) level in the blood rises in response to inflammation. This inflammation may be due to an infection.

TABLE 17

STATISTICAL ANALYSIS OF CRP LEVEL IN THE SERUM (PER PROTOCOL POPULATION)

| Variable | T Group (N = 56) | P Group (N = 55) | P value[a] |
|---|---|---|---|
| CRP (mg/L) | 3.43 (1.822) | 2.92 (1.853) | <0.0001 |

TABLE 17-continued

STATISTICAL ANALYSIS OF CRP LEVEL IN THE SERUM
(PER PROTOCOL POPULATION)

| Variable | T Group (N = 56) | P Group (N = 55) | P value[a] |
|---|---|---|---|
| at day 0 (V2) CRP (mg/L) at day 60 (V6) | 1.81 (1.095) | 3.20 (1.761) | |
| Mean Difference (SD) | −1.62 (1.854) | 0.28 (1.819) | |
| P Value[b] | <0.0001 (P) | 0.2526 (P) | |
| % Increase/ Decrease | −47.2% | 9.6% | |

P Value[a]. Compared between groups; p-value or A or Ranked ANCOVA.

P Value[b]. Compared Within groups; p-value for paired t-test or Wilcoxon signed-rank test.

CRP value was observed to be statistically significant decrement in the treatment group, whereas it was slightly increased in placebo group within the normal range. The reduction of CRP value was also found to be statistically significant between the groups over the period (p value<0.0001).

The treatment of KaraShield™ showed better results in managing the levels of inflammatory biomarker-CRP levels during general health conditions of upper respiratory tract symptoms.

Who-Quality of Life Questionnaire (WHOQOL-BREF) Score

The WHOQOL-BREF is a 26-item instrument consisting of four domains:

Physical health: 7 items (Q3, Q4, Q10, Q15, Q16, Q17, Q18)

Psychological health: 6 items (Q5, Q6, Q7, Q(8, Q19, Q26)

Social relationships: 3 items (Q20, Q21, Q24)

Environmental health: 8 items (Q8, Q9, Q12, Q13, Q14, Q23, Q24, Q25)

Note: The WHOOL-BREF has additional 2 items as generic questions. The scoring of these 2 questions was not considered in this study for the analysis as these questions were optional and not mandatory for the participants to answer.

Each individual item of the WHOQOL-BREF is scored from 1 to 5 on a response scale. An increase in the score (in a domain indicates an improvement in that domain. FIG. 11 shows items of physical domain scale of WHOQOL (BREF)

TABLE 18 (a)

STATISTICAL ANALYSIS OF WHOQOL-BREF-PHYSICAL HEALTH DOMAIN SCORE
(PER PROTOCOL POPULATION)

| | Variable | T Group (N = 56) | P Group (N = 55) | P value[a] |
|---|---|---|---|---|
| WHOQOL-BREF_PHYSICAL HEALTH DOMAIN SCORE | Physical Health Domain Score at day 0 (V2) | 23.20 (3.565) | 22.85 (3.812) | 0.6094 |
| | Physical Health Domain Score at day 7 (V3) | 23.23 (3.785) | 22.95 (3.993) | |
| | Mean Difference (SD) | 0.03 (1.348) | 0.10 (0.867) | |
| | P Value[b] | 0.6197 | 0.4540 | |
| | % Change | 0.1% | 0.4% | |
| | Physical Health Domain Score at day 0 (V2) | 23.20 (3.565) | 22.85 (3.812) | 0.0475 |
| | Physical Health Domain Score at day 15 (V4) | 23.50 (3.578) | 24.53 (3.810) | |
| | Mean Difference | 0.30 (2.696) | 1.672 (5.644) | |
| | P Value[b] | 0.3711 | 0.0160 | |
| | % Change | 1.3% | 7.4% | |
| | Physical Health Domain Score at day 0 (V2) | 23.20 (3.565) | 22.85 (3.812) | 0.8618 |
| | Physical Health Domain Score at day 30 (V5) | 24.25 (3.928) | 24.18 (3.712) | |
| | Mean Difference | 1.05 (2.489) | 1.33 (5.403) | |
| | P Value[b] | 0.0027 | 0.0643 | |
| | % Change | 4.5% | 5.8% | |
| | Physical Health Domain Score at day 0 (V2) | 23.20 (3.565) | 22.85 (3.812) | 0.0322 |
| | Physical Health Domain Score at day 60 (V6) | 25.00 (3.894) | 23.55 (3.599) | |
| | Mean Difference | 1.80 (2.672) | 0.69 (5.210) | |
| | P Value[b] | <0.0001 | 0.3897 | |
| | % Change | 7.8% | 3.1% | |

P Value[a] Compared between groups; p-value for ANCOVA or Ranked ANCOVA.

P Value[b] Compared Within groups; p-value for paired t-test or Wilcoxon signed-rank test.

TABLE 18 (b)

STATISTICAL ANALYSIS OF WHOQOL-BREF-PSYCHOLOGICAL HEALTH DOMAIN
SCORE (PER PROTOCOL POPULATION)

| | Variable | T Group (N = 56) | P Group (N = 55) | P value[a] |
|---|---|---|---|---|
| WHOQOL-BREF_PSYCHOLOGICAL HEALTH DOMAIN SCORE | Psychological Health Domain Score at day 0 (V2) | 20.73 (4.313) | 20.71 (4.241) | 0.5452 |
| | Psychological Health Domain Score at day 7 (V3) | 21.16 (3.944) | 21.09 (3.428) | |
| | Mean Difference | 0.43 (1.50) | 0.38 (2.198) | |
| | P Value[b] | 0.0187 | 0.3619 | |
| | % Change | 2.1% | 1.8% | |

TABLE 18 (b)-continued

STATISTICAL ANALYSIS OF WHOQOL-BREF-PSYCHOLOGICAL HEALTH DOMAIN
SCORE (PER PROTOCOL POPULATION)

| Variable | T Group (N = 56) | P Group (N = 55) | P value[a] |
|---|---|---|---|
| Psychological Health Domain Score at day 0 (V2) | 20.73 (4.313) | 20.71 (4.241) | 0.7036 |
| Psychological Health I Domain Score at day 15 (V4) | 22.34 (3.743) | 22.20 (3.228) | |
| Mean Difference | 1.61 (3.993) | 1.49 (4.505) | |
| P Value[b] | 0.0025 | 0.0136 | |
| % Change | 7.8% | 7.2% | |
| Psychological Health Domain Score at day 0 (V2) | 20.73 (4.313) | 20.71 (4.241) | 0.7680 |
| Psychological Health Domain Score at day 30 (V5) | 22.54 (2.789) | 22.29 (2.283) | |
| Mean Difference | 1.80 (4.469) | 1.58 (4.924) | |
| P Value[b] | 0.0037 | 0.0536 | |
| % Change | 8.7% | 7.6% | |
| Psychological Health Domain Score at day 0 (V2) | 20.73 (4.313) | 20.71 (4.241) | 0.2751 |
| Psychological Health Domain Score at day 60 (V6) | 23.20 (2.604) | 22.60 (2.705) | |
| Mean Difference | 2.46 (4.596) | 1.89 (4.995) | |
| P Value[b] | 0.0002 | 0.0107 | |
| % Change | 11.9% | 9.1% | |

P Value[a]. Compared between groups; p-value for ANCOVA or Ranked ANCOVA.

P Value[b]. Compared Within groups; p-value for paired t-test or Wilcoxon signed-rank test.

TABLE 18 (c)

STATISTICAL ANALYSIS OF WHOQOL-BREF-SOCIAL RELATIONSHIP DOMAIN
SCORE (PER PROTOCOL POPULATION)

| | Variable | T Group (N = 56) | P Group (N = 55) | P value[a] |
|---|---|---|---|---|
| WHOQOL-BREF_SOCIAL RELATIONSHIP DOMAIN SCORE | Social Relationship Domain Score at day 0 (V2) | 8.89 (2.086) | 9.05 (2.022) | 0.8036 |
| | Social Relationship Domain Score at day 7 (V3) | 9.39 (1.846) | 9.36 (1.879) | |
| | Mean Difference | 0.50 (1.829) | 0.31 (1.874) | |
| | P Value[b] | 0.0216 | 0.2909 | |
| | % Change | 5.6% | 3.4% | |
| | Social Relationship Domain Score at day 0 (V2) | 8.89 (2.086) | 9.05 (2.022) | 0.8731 |
| | Social Relationship Domain Score at day 15 (V4) | 9.63 (1.784) | 9.67 (1.836) | |
| | Mean Difference | 0.74 (2.355) | 0.62 (2.542) | |
| | P Value[b] | 0.0165 | 0.0700 | |
| | % Change | 8.3% | 6.9% | |
| | Social Relationship Domain Score at day 0 (V2) | 8.89 (2.086) | 9.05 (2.022) | 0.9976 |
| | Social Relationship Domain Score at day 30 (V5) | 9.63 (1.845) | 9.65 (1.680) | |
| | Mean Difference | 0.74 (2.49) | 0.60 (2.586) | |
| | P Value[b] | 0.0203 | 0.1020 | |
| | % Change | 8.3% | 6.6% | |
| | Social Relationship Domain Score at day 0 (V2) | 8.89 (2.086) | 9.05 (2.022) | 0.2962 |
| | Social Relationship Domain Score at day 60 (V6) | 10.32 (1.664) | 9.89 (1.960) | |
| | Mean Difference | 1.43 (2.441) | 0.84 (2.651) | |
| | P Value[b] | <0.0001 | 0.0279 | |
| | % Change | 16.1% | 9.3% | |

P Value[a]. Compared between groups; p-value for ANCOVA or Ranked ANCOVA.

P Value[b]. Compared Within groups; p-value for paired t-test or Wilcoxon signed-rank test.

TABLE 18 (d)

STATISTICAL ANALYSIS OF WHOQOL-BREF-ENVIRONMENTAL HEALTH DOMAIN
SCORE (PER PROTOCOL POPULATION)

| | Variable | T Group (N = 56) | P Group (N = 55) | P value[a] |
|---|---|---|---|---|
| WHOQOL-BREF_ENVIRONMENTAL HEALTH DOMAIN SCORE | Environmental Health Domain Score at day 0 (V2) | 17.20 (3.749) | 17.76 (3.834) | 0.0552 |
| | Environmental Health Domain Score at day 7 (V3) | 17.25 (3.543) | 18.40 (3.370) | |
| | Mean Difference | 0.05 (0.82) | 0.63 (2.818) | |
| | P Value[b] | 0.6313 | 0.1223 | |
| | % Change | 0.3% | 3.6% | |
| | Environmental Health Domain Score at day 0 (V2) | 17.20 (3.749) | 17.76 (3.834) | 0.2548 |
| | Environmental Health Domain Score at day 15 | 19.70 (4.129) | 19.18 (3.907) | |

TABLE 18 (d)-continued

STATISTICAL ANALYSIS OF WHOQOL-BREF-ENVIRONMENTAL HEALTH DOMAIN SCORE (PER PROTOCOL POPULATION)

| Variable | T Group (N = 56) | P Group (N = 55) | P value[a] |
|---|---|---|---|
| (V4) | | | |
| Mean Difference | 2.50 (3.157) | 1.42 (4.822) | |
| P Value[b] | <0.0001 | 0.0250 | |
| % Change | 14.5% | 8.0% | |
| Environmental Health Domain Score at day 0 (V2) | 17.20 (3.749) | 17.76 (3.834) | 0.0714 |
| Environmental Health Domain Score at day 30 (V5) | 20.66 (4.082) | 19.47 (3.957) | |
| Mean Difference | 3.46 (3.557) | 1.71 (5.266) | |
| P Value[b] | <0.0001 | 0.0143 | |
| % Change | 20.1% | 9.6% | |
| Environmental Health Domain Score at day 0 (V2) | 17.20 (3.749) | 17.76 (3.834) | 0.0102 |
| Environmental Health Domain Score at day 60 (V6) | 21.89 (3.888) | 19.96 (4.242) | |
| Mean Difference | 4.69 (3.991) | 2.20 (5.592) | |
| P Value[b] | <0.0001 | 0.0035 | |
| % Change | 27.3% | 12.4% | |

P Value[a]. Compared between groups; p-value for ANCOVA or Ranked ANCOVA.

P Value[b]. Compared Within groups; p-value for paired t-test or Wilcoxon signed-rank test.

Efficacy Conclusions

The present clinical study was designed to explore the comparative efficacy and safety of KaraShield™ (500 mg) in comparison to placebo (500 mg) in the management of upper respiratory tract (URT) conditions in general healthy subjects. A total of 111 subjects completed the study comprising 56 subjects from the KaraShield™ group and 55 subjects from the placebo group.

Change in the episodes of the incidences of the symptoms of upper respiratory tract conditions referring to the WURSS-24 scale was considered as primary efficacy measure of this study. Besides this, the mean symptoms score of WURSS-24 scale, Immune Status Questionnaire (ISQ), Immunoglobulin G (IgG) level in the serum, C—reactive protein (CRP) level in the serum, CD3, CD4, CD8 count in the serum and WHO Quality of Life (WHOQOL-BREF) score were considered as secondary efficacy parameters.

The per protocol (PP) population was considered for the evaluation of efficacy results. Supplementation of KaraShield™ significantly improved the status of general health immunity parameters through managing the episodes of upper respiratory tract conditions, improvement in the serum IgG level, mean ISQ raw score, symptoms score of WURSS scale, CRP level in the serum and physical domain of WHOQOL-BREF score at the end of the study period of sixty days from the baseline compared to that of the placebo.

Analysis of Safety Parameters

Vital Signs, Physical Findings & Other Observations Related to Safety

Vital signs of subjects receiving Investigational Product, or Placebo were normal, which included systolic blood pressure (SBP), diastolic blood pressure (DBP), pulse, respiratory rate and body temperature during each visit for all subjects. Physical Assessment included the systemic examination of Head & Neck, Eyes, Thyroid, ENT, Lungs/Chest, Heart, Abdomen, Musculoskeletal, Lymph Nodes and Skin at each visit. None of the subjects either receiving the Investigational Product, or Placebo had shown any abnormal result/s.

Laboratory Tests

Clinical laboratory tests were performed for all subjects for comprehensive health check-up as a part of screening and at the end of the study. The laboratory tests included haematology and biochemistry tests and routine urine analysis. Any abnormal findings were reviewed by the investigator for clinical relevance. No clinically significant changes were observed in any of the subjects during follow-up visits. All the safety parameters—whole blood tests, biochemistry and the clinical observations were found to not exhibit any statistically significant change from the start to the end of the clinical trial in both the groups.

Study Compliance

All participants were closely monitored towards the medication and visits compliance. None of the subjects discontinued and rejoined the study. There were a total of 4 subjects from the treatment group and 5 subjects from the placebo group discontinued from the study due to their respective personal reasons, but none of the subjects discontinued due to any adverse event or safety concerns. All completers had undergone all the assessments on their respective scheduled clinical visits. Missed doses were recorded in the subjects' diary cards and counts of the medication capsules were recorded for the calculation of treatment compliance. By average, 95% of the treatment compliance was observed in both the groups.

Reporting and Analysis of Adverse Events (AE) and Serious Adverse Events (SAE)/Serious Adverse Drug Reaction (ADR)

The adverse events (AE) were recorded in the respective AE forms and the observations were recorded appropriately. The study medication was well tolerated among the subjects, there were only mild adverse events observed in any of the subjects in this study which were considered not related to the study supplement. No subject withdrew from the study due to safety reasons or any adverse events related to the lab results. There was no Serious Adverse Event (SAE)/Serious Adverse Drug Reaction (ADR) reported in this study. A brief summary of the mild Adverse Events observed in the study is summarized in FIG. 12.

FIG. 12 shows adverse events.

Safety Conclusions

The study supplement contains herbs that have been in use for many years. Other preclinical and clinical studies published earlier provide further evidence of their safety.

The investigational product was found to be safe and well tolerated by the subjects. In the present study, various panels of safety parameters included vital signs assessment, adverse events reported in subjects' diary cards, adverse events reported during site visits, clinical chemistry, haematology, and urinalysis. These safety parameters were within normal range and not clinically significant. There were no serious adverse events observed in this study. Together these parameters provide further safety evidence of the product in human subjects.

Overall Conclusions

Overall, it was seen that KaraShield™ administration reduced the incidence of URI episodes, symptoms severity, and functional impairment and abilities, evaluated with the WURSS-24, in a more significant manner than the placebo. There was also a significant reduction in CRP levels in the treatment group. High CRP values are frequently found in viral or bacterial respiratory infections.

Another important factor is the strengthening of the immunity system since it plays an important role in counteracting viral infection. Hence, the immunity status was also evaluated in the clinical trial, evidencing an improvement in the ISQ score in the KaraShield™ group. In line with the latter result, an increase in IgG levels was seen in the treatment group compared to the placebo group. This is an important result since this immunoglobulin is known for playing a pivotal role in the immune system defense against viral infections, by binding the viral surface epitope, inhibiting viral entry and, thus, infection.

Altogether, the reduction of URTI episodes and symptomatology severity, and the amelioration of the immunity system by KaraShield™ resulted in improved life quality evaluated with the WHOQOL-BREF questionnaire. Hence this clinical trial demonstrated the beneficial activity of the blend of the four herbal extracts of *A. paniculata, W. somnifera, M. oleifera*, and *O. sanctum*, in reducing upper aerial tract infections in healthy subjects during 60 days of treatment. Moreover, the potential utilization of KaraShield™ in preventing URTIs is further enhanced by its safety profile. Various panels of safety parameters included vital signs assessment, adverse events reported in subjects' diary cards, adverse events notified during site visits, clinical chemistry, haematology, and urine analysis demonstrating that the investigated nutraceutical product is safe and well-tolerated. The treatment's effectiveness is seen in both self-reported questionnaires (WURSS-24, ISQ, and WHOQOL-BREF) and laboratory results (evaluation of IgG and CRP levels).

With Karashield™, improvement was observed in the management of upper respiratory tract symptoms and immunity under general health conditions. KaraShield™ may be an effective formulation in fulfilling the criteria of a supplement and may prove to be an important addition to the immunity products currently available.

While this disclosure includes specific examples, it will be apparent after an understanding of the disclosure of this application has been attained that various changes in form and details may be made in these examples without departing from the spirit and scope of the claims and their equivalents.

The invention claimed is:

1. A tablet, pill, or capsule consisting essentially of an *Andrographis paniculata* extract; a *Withania somnifera* extract; a *Moringa oleifera* extract; and an *Ocimum sanctum* extract.

2. The tablet, pill, or capsule of claim 1, wherein the *Andrographis paniculata* extract is about 25% by weight of the total tablet, pill, or capsule; the *Withania somnifera* extract is about 20% by weight of the total tablet, pill, or capsule; the *Moringa oleifera* extract is about 30% by weight of the total tablet, pill, or capsule, and the *Ocimum sanctum* extract is about 25% by weight of the total tablet, pill, or capsule.

3. The tablet, pill, or capsule of claim 1 wherein the *Andrographis paniculata* extract is about 20% to about 30% by weight of the total tablet, pill, or capsule; the *Withania somnifera* extract is about 16% to about 24% by weight of the total tablet, pill, or capsule; the *Moringa oleifera* extract is about 24% to about 36% by weight of the total tablet, pill, or capsule; and the *Ocimum sanctum* extract is about 20% to about 30% by weight of the total tablet, pill, or capsule.

4. The tablet, pill, or capsule of claim 1, wherein the tablet, pill, or capsule further consist essentially of a *Tinospora cordifolia* extract, a *Bacopa monnieri* extract, or a *Centella asiatica* extract, or combinations thereof.

5. The tablet, pill, or capsule of claim 1, wherein the *Andrographis paniculata* extract consists essentially of 10% or more of:
   (3E,4S)-3-[2-[(1R,4aS,5R,6R,8aS)-6-hydroxy-5-(hydroxymethyl)-5,8a-dimethyl-2-methylidene-3,4,4a,6,7,8-hexahydro-1H-naphthalen-1-yl]ethylidene]-4-hydroxyoxolan-2-one;
   4-[2-[(1R,4aS,5R,8aS)-5,8a-dimethyl-2-methylidene-5-[[(2R,3R,4S,5S,6R)-3,4,5-trihydroxy-6-(hydroxymethyl)oxan-2-yl]oxymethyl]-3,4,4a,6,7,8-hexahydro-1H-naphthalen-1-yl]ethyl]-2H-furan-5-one;
   4-[(E)-2-[(1R,4aS,5R,6R,8aR)-6-hydroxy-5-(hydroxymethyl)-5,8a-dimethyl-2-methylidene-3,4,4a,6,7,8-hexahydro-1H-naphthalen-1-yl]ethenyl]-2H-furan-5-one; and
   4-[2-[(1R,4aS,5R,8aS)-5-(hydroxymethyl)-5,8a-dimethyl-2-methylidene-3,4,4a,6,7,8-hexahydro-1H-naphthalen-1-yl]ethyl]-2H-furan-5-one.

6. The tablet, pill, or capsule of claim 1, wherein the *Withania somnifera* extract consists essentially of 2.5% or more of:
   (1S,2R,6S,7R,9R,11S,12S,15R,16S)-6-hydroxy-5-[(1S)-1-[(2R)-5-(hydroxymethyl)-4-methyl-6-oxo-2,3-dihydropyran-2-yl]ethyl]-2,16-dimethyl-8-oxapentacyclo[9.7.0.0$^{2,7}$.0$^{7,9}$.0$^{12,16}$]octadec-4-en-3-one;
   (1S,2S,4S,5R,10R,11S,14R,15R,18S)-5-hydroxy-15-[(1S)-1-[(2R)-5-(hydroxymethyl)-4-methyl-6-oxo-2,3-dihydropyran-2-yl]ethyl]-10,14-dimethyl-3-oxapentacyclo[9.7.0.0$^{2,4}$.0$^{5,10}$.0$^{14,18}$]octadec-7-en-9-one; and
   (1S,2S,4S,5R,10R,11S,14S,15S,18S)-15-[(1R)-1-[(2R)-4,5-dimethyl-6-oxo-2,3-dihydropyran-2-yl]-1-hydroxyethyl]-5-hydroxy-10,14-dimethyl-3-oxapentacyclo[9.7.0.0$^{2,4}$.0$^{5,10}$.0$^{14,18}$]octadec-7-en-9-one.

7. The tablet, pill, or capsule of claim 1, wherein the *Ocimum sanctum* extract consists essentially of 1% or more of:
   (1S,2R,4aS,6aR,6aS,6bR,8aR,10S,12aR,14bS)-10-hydroxy-1,2,6a,6b,9,9,12a-heptamethyl-2,3,4,5,6,6a,7,8,8a,10,11,12,13,14b-tetradecahydro-1H-picene-4a-carboxylic acid.

8. The tablet, pill, or capsule of claim 1, wherein the *Andrographis paniculata* extract consists essentially of 10% or more of:
   (3E,4S)-3-[2-[(1R,4aS,5R,6R,8aS)-6-hydroxy-5-(hydroxymethyl)-5,8a-dimethyl-2-methylidene-3,4,4a,6,7,8-hexahydro-1H-naphthalen-1-yl]ethylidene]-4-hydroxyoxolan-2-one;
   4-[2-[(1R,4aS,5R,8aS)-5,8a-dimethyl-2-methylidene-5-[[(2R,3R,4S,5S,6R)-3,4,5-trihydroxy-6-(hydroxymethyl)oxan-2-yl]oxymethyl]-3,4,4a,6,7,8-hexahydro-1H-naphthalen-1-yl]ethyl]-2H-furan-5-one;

4-[(E)-2-[(1R,4aS,5R,6R,8aR)-6-hydroxy-5-(hydroxymethyl)-5,8a-dimethyl-2-methylidene-3,4,4a,6,7,8-hexahydro-1H-naphthalen-1-yl]ethenyl]-2H-furan-5-one; and 4-[2-[(1R,4aS,5R,8aS)-5-(hydroxymethyl)-5,8a-dimethyl-2-methylidene-3,4,4a,6,7,8-hexahydro-1H-naphthalen-1-yl]ethyl]-2H-furan-5-one; and the *Withania somnifera* extract comprises 2.5% or more of:

(1S,2R,6S,7R,9R,11S,12S,15R,16S)-6-hydroxy-15-[(1S)-1-[(2R)-5-(hydroxymethyl)-4-methyl-6-oxo-2,3-dihydropyran-2-yl]ethyl]-2,16-dimethyl-8-oxapentacyclo[9.7.0.0$^{2,7}$.0$^{7,9}$.0$^{12,16}$]octadec-4-en-3-one;

(1S,2S,4S,5R,10R,11S,14R,15R,18S)-5-hydroxy-15-[(1S)-1-[(2R)-5-(hydroxymethyl)-4-methyl-6-oxo-2,3-dihydropyran-2-yl]ethyl]-10,14-dimethyl-3-oxapentacyclo[9.7.0.0$^{2,4}$.0$^{5,10}$.0$^{14,18}$]octadec-7-en-9-one;

(1S,2S,4S,5R,10R,11S,14S,15S,18S)-15-[(1R)-1-[(2R)-4,5-dimethyl-6-oxo-2,3-dihydropyran-2-yl]-1-hydroxyethyl]-5-hydroxy-10,14-dimethyl-3-oxapentacyclo[9.7.0.0$^{2,4}$.0$^{5,10}$.0$^{14,18}$]octadec-7-en-9-one; and the *Ocimum sanctum* extract comprises 1% or more of:

(1S,2R,4aS,6aR,6aS,6bR,8aR,10S,12aR,14bS)-10-hydroxy-1,2,6a,6b,9,9,12a-heptamethyl-2,3,4,5,6,6a,7,8,8a,10,11,12,13,14b-tetradecahydro-1H-picene-4a-carboxylic acid.

9. A method of treating an influenza viral infection in a human in need thereof consisting essentially of administering a therapeutically effective amount of the tablet, pill, or capsule of claim 1 to the human in need thereof to effectively treat the influenza viral infection in said human.

10. The method of claim 9, wherein the therapeutically effective amount is a dosage of between about 100 mg per day and 2000 mg per day.

11. The method of claim 9, wherein the therapeutically effective amount is a dosage of about 500 mg per day.

\* \* \* \* \*